United States Patent [19]
Lappi et al.

[11] Patent Number: 5,916,772
[45] Date of Patent: Jun. 29, 1999

[54] RECOMBINANT PRODUCTION OF SAPORIN-CONTAINING PROTEINS

[75] Inventors: Douglas A. Lappi, Del Mar, Calif.; Isabel Barthelemy, Madrid, Spain; J. Andrew Baird; Barbara A. Sosnowski, both of San Diego, Calif.

[73] Assignee: Whittier Institute for Diabetes and Endocrinology, La Jolla, Calif.

[21] Appl. No.: 08/356,161

[22] PCT Filed: Jun. 14, 1993

[86] PCT No.: PCT/US93/05702

§ 371 Date: Apr. 13, 1995

§ 102(e) Date: Apr. 13, 1995

[87] PCT Pub. No.: WO93/25688

PCT Pub. Date: Dec. 23, 1993

Related U.S. Application Data

[63] Continuation-in-part of application No. 07/901,718, Jun. 16, 1992, abandoned.

[51] Int. Cl.$^6$ .............................. C12P 21/04; C12N 15/62
[52] U.S. Cl. ................. 435/69.7; 435/69.4; 435/252.33; 435/320.1; 536/23.4
[58] Field of Search ................................ 435/69.1, 69.4, 435/69.7, 252.33, 320.1; 536/23.4

[56] References Cited

U.S. PATENT DOCUMENTS

| | | | |
|---|---|---|---|
| 4,468,382 | 8/1984 | Bacha et al. | 424/177 |
| 4,785,079 | 11/1988 | Gospodarowicz et al. | 530/399 |
| 4,962,188 | 10/1990 | Frankel | 530/389 |
| 5,087,616 | 2/1992 | Myers et al. | 514/21 |
| 5,116,753 | 5/1992 | Beattie et al. | 435/240.2 |
| 5,120,715 | 6/1992 | Kato et al. | 514/21 |
| 5,155,214 | 10/1992 | Baird et al. | 530/399 |
| 5,169,933 | 12/1992 | Anderson et al. | 530/391.3 |
| 5,175,147 | 12/1992 | Folkman et al. | 514/12 |
| 5,191,067 | 3/1993 | Lappi et al. | 530/399 |

FOREIGN PATENT DOCUMENTS

| | | |
|---|---|---|
| 259 904 | 3/1988 | European Pat. Off. . |
| 341 904 A2 | 5/1989 | European Pat. Off. . |
| 402 544 A1 | 12/1990 | European Pat. Off. . |
| 466 222 | 1/1992 | European Pat. Off. . |
| 2216891 | 10/1989 | United Kingdom . |
| WO 85/03508 | 8/1985 | WIPO . |
| WO 90/12597 | 11/1990 | WIPO . |
| WO 91/11459 | 8/1991 | WIPO . |
| WO 91/18099 | 11/1991 | WIPO . |
| WO 92/04918 | 4/1992 | WIPO . |

OTHER PUBLICATIONS

Bacha et al., "Interleukin 2 Receptor–Targeted Cytotoxicity," *J. Exp. Med.* 167(2):612–622, 1988.

Baird et al., "Angiogenic factor in human ocular fluid," *The Lancet* (Sep. 7): 563, 1985.

Baird et al., "Molecular characterization of fibroblast growth factor: Distribution and biological activities in various tissues," *Recent Progress in Hormone Research* 42: 143–205, 1986.

Baird et al., "Receptor– and heparin–binding domains of basic fibroblast growth factor," *Proc. Natl. Acad. Sci. U.S.A.* 85: 2324–2328, 1988.

Baird et al., "Fibroblast growth factors," *British Med. Bull.* 45(2): 438–452, 1989.

Baird et al., "Biological and chemical characterization of basic FGF–saporin mitoxin," *J. Cell Biol. Abstracts* 11(5): 173a, abstract #745, 1990.

Barbieri and Stirpe, "Ribosome–inactivating proteins from plants: Properties and possible uses," *Cancer Surveys* 1(3): 489–520, 1982.

Barbieri et al., "Blood clearance and organ distribution and tissue concentration of native, homopolymerized and Ig–G–conjugated ribosome–inactivating proteins," *Xenobiotica* 20(12): 1331–1341, 1990.

Barr et al., "Expression and processing of biologically active fibroblast growth factors in the yeast *Saccharomyces cerevisiae*," *J. Biol. Chem.* 263(31): 16471–16478, 1988.

Barra et al., "Assessment of sequence features in internal regions of proteins," *Biotech. and Applied Biochem.* 13:48–53, 1991.

Beattie et al., "Selective elimination of fibroblasts from pancreatic islet monolayers by basic fibroblast growth factor–saporin mitotoxin," *Diabetes* 39(8): 1002–1005, 1990.

Beattie et al., "Functional Impact of Attachment and Purification in the Short Term Culture of Human Pancreatic Islets," *Journal of Clinical Endocrinology and Metabolism* 73(1): 93–98, 1991.

Beitz et al., "Antitumor activity of basic fibroblast growth factor–saporin mitotoxin in vitro and in vivo," *Cancer Research* 52: 227–230, 1992.

Benatti et al., "Nucleotide sequence of cDNA coding for saporin–6, a type–1 ribosome–inactivating protein from *Saponaria officinalis*," *Eur. J. Biochem.* 183: 465–470, 1989.

(List continued on next page.)

*Primary Examiner*—Keith D. Hendricks
*Attorney, Agent, or Firm*—Seed and Berry LLP

[57] ABSTRACT

Methods for the recombinant production of saporin-containing proteins, including cell surface binding protein-saporin fusion proteins, are provided. The resulting fusion proteins are cytotoxic to targeted cells. In preferred embodiments, methods are provided for the production of basic fibroblast factor (bFGF)-saporin fusion proteins by culturing *Escherichia coli* that has been transformed with a vector containing DNA encoding bFGF linked via a spacer peptide to the amino terminus of a cytotoxic portion of a saporin polypeptide to obtain expression of the DNA, and isolating the resulting FGF-saporin fusion protein. FGF-saporin fusion proteins and saporin proteins containing from about 5 to 12 amino acid N-terminal extensions are also provided.

23 Claims, No Drawings

OTHER PUBLICATIONS

Better et al., "Expression of engineering antibodies and antibody fragments in microorganisms," *Methods in Enzymology* 178: 476–496, 1989.

Casscells et al., "Elimination of smooth muscle cells in experimental restenosis: Targeting of fibroblast growth factor receptors," *Proc. Natl. Acad. Sci. U.S.A.* 89:7159–7163, 1992.

Chaudhary et al., "Activity of recombinant fusion protein between transforming growth factor type α and Pseudomonas toxin," *Proc. Natl. Acad. Sci. U.S.A.* 84: 4538–4542, 1987.

Chaudhary et al., "Selective killing of HIV–infected cells by recombinant human CD4–Pseudomonas exotoxin hybrid protein," *Nature* 335: 369–372, 1989.

Duffaud et al., "Expression and secretion of foreign proteins in *Escherichia coli*," *Methods in Enzymology* 153: 492–507, 1987.

Eriksson et al., "Three–dimensional structure of human basic fibroblast growth factor," *Proc. Natl. Acad. Sci. U.S.A.* 88:3441–3445, 1991.

Esch et al., "Primary structure of bovine brain acidic fibroblast growth factor (FGF)," *Biochem. and Biophys. Res. Comm.* 133(2): 554–562, 1985.

Esch et al., "Primary structure of bovine pituitary basic fibroblast growth factor (FGF) and comparison with the amino–terminal sequence of bovine brain acidic FGF," *Proc. Natl. Acad. Sci. U.S.A.* 82: 6507–6511, 1985.

Folkman and Klagsbrun, "Angiogenic factors," *Science* 235: 442–447, 1987.

Fordham–Skelton et al., "Synthesis of saporin gene probes from partial protein sequence data: Use of inosine–oligonucleotides, genomic DNA and the polymerase chain reaction," *Mol. Gen. Genet.* 221:134–138, 1990.

Fordham–Skelton et al., "Characterization of saporin genes: in vitro expression and ribosome inactivation," *Mol. Gen. Genet.* 229: 460–466, 1991.

Fox et al., "Production, biological activity, and structure of recombinant basic fibroblast growth factor and an analog with cysteine replaced by serine," *J. Biol. Chem.* 263(34): 18452–18458, 1988.

Gelfi et al., "Isoelectric focusing in immobilized pH gradients in the pH 10–11 range," *J. Biochem. and Biophys. Methods* 15: 41–48, 1987.

Gospodarowicz et al., "Isolation of brain fibroblast growth factor by heparin–Sepharose affinity chromatography: Identity with pituitary fibroblast growth factor," *Proc. Natl. Acad. Sci. U.S.A.* 81: 6963–6967, 1984.

Habuka et al., "Expression and Secretion of Mirabilis Antiviral Protein in *E. coli* and its inhibition of in vitro Eukaryotic and Prokaryotic protein synthesis," *J. Biol. Chem.* 265(19): 10988–10992, 1989.

Hartley et al., "Single–chain ribosome inactivating proteins from plants depurinate *Escherichia coli* 23S ribosomal RNA," *FEBS* 290(1,2):65–68, 1991.

Hertler and Frankel, "Immunotoxins: A clinical review of their use in the treatment of malignancies," *J. Clinical Oncology* 7(12): 1932–1942, 1989.

Imamura et al., "Purification of basic FGF receptors from rat brain," *Biochem. and Biophys. Res. Comm.* 155(2): 583–590, 1988.

Kataoka, "DNA sequence of Mirabilis Antiviral Protein (MAP), a ribosome–inactivating protein with an antiviral property, from *Mirabilis jalapa* L. and its expression in *Escherichia coli*," *J. Biol. Chem.* 266(13): 8426–8430, 1991.

Kelley et al., "Interleukin 2–diphtheria toxin fusion protein can abolish cell–mediated immunity in vivo," *Proc. Natl. Acad. Sci. U.S.A.* 85: 3980–3984, 1989.

Lambert et al., "Purified immunotoxins that are reactive with human lymphoid cells," *J. Biol. Chem.* 260(22): 12035–12041, 1985.

Lambert et al., "Immunotoxins containing single chain ribosome–inactivating proteins," *Cancer Treatment Res.* 37: 175–209, 1988.

Lappi and Baird, "Mitotoxins: Growth factor–targeted cytotoxic molecules," *Progress in Growth Factor Res.* 2: 223–236, 1990.

Lappi et al., "The disulfide bond connecting the chains of ricin," *Proc. Natl. Acad. Sci. U.S.A.* 75(3): 1096–1100, 1978.

Lappi et al., "Characterization of a *Saponaria officinalis* seed ribosome–inactivating protein: Immunoreactivity and sequence homologies," *Biochem. and Biophys. Research Comm.* 129(3): 934–942, 1985.

Lappi et al., "Biological and chemical characterization of basic FGF–saporin mitoxin," *Biochem. and Biophys. Research Comm.* 160(2): 917–923, 1989.

Lappi et al., "Basic fibroblast growth factor–saporin mitotoxin: an endothelial cell growth inhibitor," *1990 UCLA Symposia Abstract, 19th Annual UCLA Symposia on Molecular and Cellular Biology*, Keystone, Colorado, Apr. 6–12, 1990.

Lappi et al., "The basic fibroblast growth factor–saporin mitotoxin acts through the basic fibroblast growth factor receptor," *J. Cell. Physio.* 147: 17–26, 1991.

Lappi et al., "Basic fibroblast growth factor in cells derived from Dupuytren's contracture: Synthesis, presence, and implications for treatment of the disease," *J. Hand Surgery* 17A(2): 324–332, 1992.

Lappi, D., "Reducing the heterogeneity of chemically conjugated targeted toxins: homogeneous basic FGF–saporin," *Anal. Biochem.* 212: 446–451, 1993.

Lindner et al., "Role of basic fibroblast growth factor in vascular lesion formation," *Circulation Research* 68(1): 106–113, 1991.

Maras et al., "The amino acid sequence of a ribosome–inactivating protein from *Saponaria officinalis* seeds," *Biochemistry International* 21(5): 831–838, 1990.

Marcucci et al., "In vivo effects in mice of an anti–T cell immunotoxin," *J. Immunology* 142: 2955–2960, 1989.

Montecucchi et al., "N–terminal sequence of some ribosome–inactivating proteins," *Int. J. Peptide Protein Res.* 33: 263–267, 1989.

Moscatelli, D., "High and low affinity binding sites for basic fibroblast growth factor on cultured cells: Absence of a role for low affinity binding in the stimulation of plasminogen actirator production by bovine capillary endothelial cells," *J. Cell. Physiol.* 131:123–130, 1987.

Nuefeld and Gospodarowicz, "The identification and partial characterization of the fibroblast growth factor receptor of baby hamster kidney cells," *J. Biol. Chem.* 260(25): 13860–13868, 1985.

O'Hare et al., "Cytotoxicity of a recombinant ricin–A–chain fusion protein containing a proteolytically–cleavable spacer sequence," *FEBS Lett.* 273: 260–264, 1990.

Oeltmann and Frankel, "Advances in immunotoxins," *FASEB J. 5:* 2334–2337, 1991.

Ogata et al., "Cytotoxic activity of a recombinant fusion protein between interleukin 4 and Pseudomonas exotoxin," *Proc. Natl. Acad. Sci. U.S.A. 86:* 4215–4219, 1989.

Pettmann et al., "Biologically Active Basic Fibroblast Growth Factor Migrates at 27kD in 'Non–Denaturing' SDS–Polyacrylamide Gel Electrophoresis," *Growth Factors 5:209–220*, 1991.

Prieto et al., "Expression and characterization of basic FGF–Saporin in *E. coli*," Abstract presented at the meetings, "The Fibroblast Growth Factor Family," La Jolla, California, Jan. 16–18 and the 20th UCLA Symposia on Molecular and Cellular Biology, Keystone, Colorado, Apr. 1–7, 1991.

Prieto et al., "Expression and characterization of a basic fibroblast growth factor–saporin fusion protein in *Escherichia coli*," *Annals N.Y. Acad. Sci. 638:* 434–437, 1991.

Seno et al., "Stabilizing basic fibroblast growth factor using protein engineering," *Biochem. and Biophys. Res. Comm. 151(2):* 701–708, 1988.

Siegall et al., "Cytotoxic activity of an interleukin 6–Pseudomonas exotoxin fusion protein on human myeloma cells," *Proc. Natl. Acad. Sci. U.S.A. 85:* 9738–9742, 1988.

Siegall et al., "Cytotoxic activities of a fusion protein comprised of TGFα and Pseudomonas exotoxin," *FASEB J. 3:* 2647–2652, 1989.

Siegall et al., "Cytotoxic activity of chimeric proteins composed of acidic fibroblast growth factor and Pseudomonas exotoxin on a variety of cell types," *FASEB J. 5:* 2843–2849, 1991.

Siena et al., "Synthesis and characterization of an antihuman T–lymphocyte saporin immunotoxin (OKT1–SAP) with in vivo stability into nonhuman primates," *Blood 72(2):*756–765, 1988.

Soria, M., "Immunotoxins, ligand–toxin conjugates and molecular targeting," *Pharmacological Research 21(2):* 35–46, 1989.

Tazzari et al., "Ber–H2 (anti–CD30)–saporin immunotoxin: a new tool for the (sic) treatment of Hodgkin's disease and CD30+ lymphoma: in vitro evaluation," *Brit. J. Haematology 81:* 203–211, 1992.

Thompson and Fiddes, "Chemical characterization of the cysteines of basic fibroblast growth factor," *Annals N.Y. Acad. Sci. 638:* 78–88, 1991.

Thorpe et al., *J. Natl. Cancer Inst. 75:* 151–159, 1985.

von Heijne, "Signal sequences: the limits of variation," *J. Mol. Biol. 184:* 99–105, 1985.

Zhang et al., "Three–dimensional structure of human basic fibroblast growth factor, a structural homolog of interleukin 1β," *Proc. Natl. Acad. Sci. U.S.A. 88:* 3446–3450, 1991.

RECOMBINANT PRODUCTION OF SAPORIN-CONTAINING PROTEINS

This application is a continuation-in-part of U.S. application Ser. No. 07/901,718, filed Jun. 16, 1992, by Douglas A. Lappi, Isabel Barthelemy, and Andrew J. Baird entitled "RECOMBINANT PRODUCTION OF SAPORIN-CONTAINING PROTEINS" now abandoned. The disclosure of U.S. application Ser. No. 07/901,718 is incorporated herein in its entirety by reference. This is also a 371 of PCT/US93/05702, filed Jun. 14, 1993.

FIELD OF THE INVENTION

The present invention relates to the recombinant production of proteins and more particularly to the recombinant production of saporin and saporin-containing fusion proteins.

BACKGROUND OF THE INVENTION

Ribosome-inactivating-proteins (RIPs) are plant proteins that catalytically inactivate eukaryotic ribosomes. RIPS have been shown to inactivate ribosomes by interfering with the protein elongation step of protein synthesis. For example, the RIP saporin (SAP) has been shown to inactivate 60S ribosomes by cleavage of the n-glycosidic bond of the adenine at position 4324 in the rat 28S ribosomal RNA (rRNA). This particular region in which $A^{4324}$ is located in the rRNA is highly conserved among prokaryotes and eukaryotes. $A^{4324}$ in 28S rRNA corresponds to $A^{2660}$ in *Escherichia coli* (*E. coli*) 23S rRNA. Several RIP's also appear to interfere with protein synthesis in prokaryotes, such as *E. coli*. Since RIPs are toxic to eukaryotic cells and some RIPs are toxic to prokaryotes (see, e.g., Habuka et al. (1990) *J. Biol. Chem.* 265:10988–10992), they are difficult to express using recombinant DNA methodologies.

Several structurally related RIP's have been isolated from seeds and leaves of the plant *Saponaria officinalis* (soapwort). Among these, saporin-6 is the most active and abundant, representing 7% of total seed proteins. Saporin is very stable, has a high isoelectric point, does not contain carbohydrates, and is resistant to denaturing agents, such as SDS, and a variety of proteases. The amino acid sequences of several saporin-6 isoforms from seeds are known and there appear to be families of saporin RIPs differing in few amino acid residues.

Because saporin is a type I RIP, it does not possess a cell-binding chain, like the toxins ricin and abrin. Consequently, its toxicity to whole cells is much lower than the toxins. When targeted to cells so that it is internalized by the cells, however, its cytotoxicity is 100- to 1000-fold more potent than ricin A chain. Because of its cytotoxicity, saporin has been covalently linked to cell surface binding ligands to produce cytotoxic chemical-conjugates or linked to antibodies to produce immunotoxins that are targeted to, and internalized by, specific cells (see, e.g., Soria (1989) *Pharmacological Res.* 21(Supp 2):35–46, at 36). For example, basic fibroblast growth factor (bFGF) has been chemically conjugated to saporin-6 to produce the mitoxin FGF-SAP (see, e.g., U.S. Pat. No. 5,191,067 to Lappi et al.; and Lappi et al. (1989) *Biochem. and Biophys. Res. Comm.* 160:917–923). FGF-saporin conjugates have been used to treat restinosis (see, e.g., International Patent Application No. WO 92/11872, which is based in U.S. application Ser. No. 07/637,074). Treatment is effected by local or intravenous administration of a therapeutically effective amount of the FGF conjugate following, for example, balloon angioplasty. FGF-saporin conjugates also have shown promise as agents for the treatment of certain tumors. The growth of melanomas and other tumors that express receptors to which FGF binds can be inhibited by FGF-SAP (see, e.g., International Application No. WO 92/04918, which is based on U.S. patent application Ser. No. 07/585,319: and Beitz et al. (1992) *Cancer Research* 52:227–230).

An anti-human immunoglobulin heavy chain monoclonal antibody has been conjugated to saporin-6. The resulting immunotoxin is potentially useful for eliminating lymphoma and leukemia cells from human bone marrow during ex vivo treatment prior to reimplantation. Other chemical conjugates of saporin with a panel of anti-T lymphocyte monoclonal antibodies have shown promise as ex vivo agents for purging human bone marrow prior to transplantation, and as systemic therapeutic agents in patients with graft-versus-host disease and T-cell and B-cell leukemia.

Presently, conjugation of saporin to cell binding ligands and antibodies has been effected chemically. Chemical conjugation, however, results in a heterogeneous population of molecules. For example, bFGF is conjugated via a cysteine residue to saporin, which is first derivatized with N-succinimdyl-3(2-pyridyldithio)propionate(SPDP). Basic FGF has at least two cysteines available for reaction with SPDP-derivatized saporin. Consequently, reaction of the bFGF with the SPDP-derivatized SAP results in an array of molecules, which probably differ with respect to biologically relevant properties and may not be ideal for in vivo applications.

In view of the many potential applications for saporin-containing fusion proteins, efficient recombinant means for the direct production of uniform preparations of saporin-containing proteins would be of great value. Because of the toxic effect of saporin on *E. coli*, as well as eukaryotes, recombinant production of biologically active saporin has, thus far, been elusive. DNA encoding saporin-6 has been cloned and a DNA encoding truncated form expressed in *E. coli* (U.K. Patent Application GB 2216891 A to FARMITALIA). The resulting protein, however, is not cytotoxic. DNA encoding recombinant bFGF-saporin fusion proteins in which the saporin and FGF are truncated have been prepared (see, Prieto et al. (1991) *Ann. N.Y. Acad. Sci.* 538:434–437). The resulting fusion protein, however, was subsequently found not to be cytotoxic.

Therefore, it is an object herein to provide effective recombinant DNA methods for the production of cytotoxic saporin-containing proteins, including fusion proteins, in prokaryotic cells. It is also an object herein to provide bFGF-SAP conjugates that are produced by recombinant DNA methods.

SUMMARY OF THE INVENTION

DNA constructs encoding saporin-containing proteins are provided. The DNA encodes saporin-containing proteins. The saporin-containing proteins are made of an N-terminal extension linked to the amino terminus of a saporin protein. The saporin polypeptide includes at least as much of a saporin protein as needed for the saporin to exhibit cytoxicity or protein synthesis inhibition in selected assays. The DNA encoding saporin and DNA encoding the N-terminal extension are selected such that saporin-containing protein is cytotoxic upon internalization by selected cells.

The N-terminal extension appears to render the resulting saporin-containing protein sufficiently non-cytotoxic to a host to permit recombinant expression, including translation of the saporin-containing peptide in a selected host. In some embodiments, the N-terminal extension is about two to fifteen, preferably five to twelve amino acids. The sequence of the N-terminal extension can be the same as the sequence of the native saporin polypeptide signal sequence.

In other embodiments, the N-terminal extension is a ligand, such as a cell surface binding protein or antibody, that specifically interacts with proteins on the surfaces of targeted cells. The DNA encoding the ligand is linked to the DNA encoding the N-terminus of the saporin polypeptide or via one, preferably two, or more codons that encode a linking peptide or amino acid. The number of linking codons is selected such that the resulting DNA encodes a fusion protein that is cytotoxic to selected cells.

The combination of the ligand and saporin is prepared as a chimera, using recombinant DNA techniques. The fusion protein molecule is designed and produced in such a way that the receptor-binding domain of the ligand moiety of the complex is available for recognition of its respective cell-surface receptor and can target the fusion protein to cells containing its respective cell-surface receptor. In a preferred embodiment, the ligand is either basic FGF or another FGF polypeptide, such as acidic FGF, that is reactive with the high affinity FGF receptor.

The fusion proteins containing the ligand linked to a saporin polyptide via a peptide spacer region are also provided. The spacer region contains one or more amino acids, such that the resulting fusion protein has the desired cytotoxic activity. In preferred embodiments, the ligand is an FGF. The fusion proteins are potent cytotoxic agents and, thus, should be useful in treating a variety of FGF-mediated pathophysiological conditions, including conditions for which chemically conjugated FGF-SAP has been demonstrated to be effective.

Vectors or plasmids for expression of the DNA encoding the saporin-containing proteins are also provided. Vectors or plasmids that include a selectable marker gene and an origin of replication functional in the selected host, such as a bacterial, yeast, insect or mammalian cells or the expression of the fusion proteins are provided. In preferred embodiments the plasmids are suitable for expression of heterologous proteins in prokaryotic hosts, such as *E. coli*. The DNA encoding the saporin-containing protein is operatively linked to a promoter region such that the DNA is inducibly expressed in the selected host. In other preferred embodiments, the DNA construct is operatively linked to a transcription terminator that functions to terminate transcription of the DNA encoding the saporin-containing protein in the selected host. Preferred hosts are those that effect inducible expression of the DNA construct.

Methods for expression of the DNA constructs that encode the saporin-containing proteins are provided. In particular, methods are provided for the production of saporin-containing proteins in *E. coli* by transforming the *E. coli* host cell with a plasmid containing the DNA construct encoding an N-terminal extension linked to the amino terminus of a cytotoxic portion of a saporin polypeptide to obtain expression of the DNA, and isolating the saporin-containing protein.

In preferred embodiments, a DNA construct encoding saporin linked to all or a portion of its native signal sequence is inserted into a plasmid such that the DNA construct is operatively linked to a signal sequence that functions in *E. coli* to direct secretion of the linked peptide and is operatively linked to an inducible promoter and a terminator functional in the selected host. The plasmid is introduced into a host in which the promoter is inducibly regulated. In other preferred embodiments, the DNA constructs include encoding a saporin polypeptide is linked to DNA encoding a FGF.

In most preferred embodiments, DNA constructs and methods for producing fusion proteins containing bFGF linked to saporin are provided. The fusion proteins are targeted to and are cytotoxic upon internalization by cells that contain cell surface receptors to which the bFGF in the fusion protein binds.

DETAILED DESCRIPTION OF THE PREFERRED EMBODIMENTS

Definitions

Unless defined otherwise, all technical and scientific terms used herein have the same meaning as is commonly understood by one of skill in the art to which the subject matter herein belongs. All U.S. patents and all publications mentioned herein are incorporated in their entirety by reference thereto.

The amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, saporin (abbreviated herein as SAP) refers to polypeptides having amino acid sequences found in the natural plant host *Saponaria officinalis*, as well as modified sequences, having amino acid substitutions, deletions, insertions or additions, which still express substantial ribosome-inactivating activity. Purified preparations of saporin are frequently observed to include several molecular isoforms of the protein. It is understood that differences in amino acid sequences can occur in saporin from different species as well as between saporin molecules from individual organisms of the same species.

Thus, as used herein, a saporin polypeptide includes any of the isoforms of saporin that may be isolated from *Saponaria officinalis* or related species or modified form that retain cytotoxic activity. In particular, such modified saporin may be produced by modifying the DNA disclosed herein by altering one or more amino acids or deleting or inserting one or more amino acids, such as a cysteine that may render it easier to conjugate to FGF or other cell surface binding protein. Any such protein, or portion thereof, that, when conjugated to FGF as described herein, that exhibits cytoxicity in standard in vitro or in vivo assays within at least about an order of magnitude of the saporin conjugates described herein is contemplated for use herein.

As used herein, saporin-containing proteins are either: (1) proteins that include a saporin protein and an N-terminal extension that does not confer additional biological activities on the the saporin; or (2) fusion proteins containing a saporin polypeptide and a ligand, preferably basic fibroblast growth factor (bFGF), that is reactive with a particular cell surface receptor.

The resulting saporin proteins (1) are useful as toxins for chemical conjugation to various ligands of cell surface receptors, such as growth factors (e.g. fibroblast growth factor), hormones, antibodies, and the like. The resulting saporin-containing fusion proteins (2) are useful as cytotoxins for treating diseases, including, but not limited to, certain restinosis and cancers, such as human melanomas and human ovarian carcinomas.

As used herein DNA fragment, refers to a DNA molecule that is not part of a chromosome or DNA of an organelle, other than a man-made plasmid or vector. DNA fragments can include origins of DNA replication, prokaryotic and eukaryotic genes from various sources, such as selectable marker genes, repressor genes, and any other sequence of nucleotides. The DNA fragment may be in the circular form of a plasmid vector.

As used herein, a mitoxin is a cytotoxic molecule targeted to specific cells by a mitogen.

As used herein, to target a saporin-containing protein means to direct it to a cell that expresses a selected receptor. Upon binding to the receptor the saporin-containing protein is internalized by the cell and is cytotoxic to the cell.

As used herein, the term biologically active, or reference to the biological activity of a saporin-containing polypeptide or cytotoxicity of a saporin-containing polypeptide, refers to the ability of such polypeptide to inhibit protein synthesis by inactivation of ribosomes either in vivo or in vitro or to inhibit the growth of or kill cells upon internalization of the saporin-containing polypeptide by the cells. Preferred biologically active saporin polypeptides are those that are toxic to eukaryotic cells upon entering the cells. Such biological or cytotoxic activity may be assayed by any method known to those of skill in the art including, but not limited to, the in vitro assays that measure protein synthesis and in vivo assays that assess cytoxicity by measuring the effect of a test compound on cell proliferation or on protein synthesis. Particularly preferred, however, are assays that assess cytoxicity in targeted cells.

As used herein, secretion signal refers to a peptide region within the precursor protein that directs secretion of the precursor protein from the cytoplasm of the host into the periplasmic space or into the extracellular growth medium. Such signals may be either at the amino terminus or carboxyl terminus of the precursor protein. The preferred secretion signal is linked to the amino terminus of the N-terminal extension region.

As used herein, N-terminal extension, refers to a peptide region that is linked to the amino terminus of a biologically active portion of a saporin polypeptide. As demonstrated herein, the N-terminal extension serves to render the saporin polypeptide portion of the saporin-containing protein either nontoxic to the host upon expression of the protein in the host or substantially less toxic to the host than the expression of a saporin polypeptide without a N-terminal extension. N-terminal extensions having as few as 5 amino acids, and as many as 500 amino acids (or more depending on the size of the ligand used) can be employed. Presently preferred N-terminal extension regions are in the range of about 8 to 300 amino acids. Most preferred N-terminal extension regions have in the range of about 5 to about 150 amino acids. Particularly preferred N-terminal extensions encode ligands.

As used herein, ligand refers to any polypeptide that is capable of binding to a cell-surface protein and is capable of facilitating the internalization of the ligand-containing fusion protein into the cell. Such ligands include growth factors, antibodies or fragments thereof, hormones, and other types of proteins.

As used herein, FGF refers to polypeptides having amino acid sequences of native FGF proteins, as well as modified sequences, having amino acid substitutions, deletions, insertions or additions of the native protein but retaining the ability to bind to FGF receptors and to be internalized. Such polypeptides include, but are not limited to, FGF-1–FGF-9. For example, bFGF should be generally understood to refer to polypeptides having substantially the same amino acid sequences and receptor-targeting activity as that of bovine bFGF or human bFGF.

It is understood that differences in amino acid sequences can occur among FGFs of different species as well as among FGFs from individual organisms or species. Reference to FGFs is also intended to encompass proteins isolated from natural sources as well as those made synthetically, as by recombinant means or possibly by chemical synthesis. FGF also encompasses muteins of FGF that possess the ability to target saporin to FGF-receptor expressing cells. Such muteins include, but are not limited to, those produced by replacing one or more of the cysteines with serine or other amino acid or by replacing any of the amino acids (see, e.g., U.S. Pat. No. 5,120,715 to Kato et al.; U.S. Pat. No. 5,175,147 to Folkman et al.; European Patent Application 510662 A to TAKEDA CHEMICAL INDUSTRIES LTD.; JP 4164096 A to TAKEDA CHEMICAL INDUSTRIES LTD) in order to, for example, retain or increase the activity or stability of the growth factor, to reduce or eliminate disulfide scrambling, or to alter glycosylation As used herein, the term "FGF receptor" is used to refer to receptors that specifically interact with FGF and transport it into the cell. Included among these are the receptors described in International Application No. WO 91/00916, which is based on U.S. patent application Ser. No.07/377, 033; International Application No. WO 92/00999, which is based on U.S. patent application Ser. No.07/549,587; International Application No. WO 90/05522; and International Application No. WO 92/12948; see, also Imamura (1988) *Biochem. Biophys. Res. Comm.* 155:583–590 and Moscatelli (1987) J. Cell. Physiol. 131:123–130.

As used herein, the term "polypeptide reactive with the FGF receptor" refers to any polypeptide that specifically interacts with FGF receptor, preferably the high-affinity FGF receptor, and is transported into the cell by virtue of its interaction with the FGF receptor.

As used herein, operative linkage or operative association of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, a promoter region refers to the portion of DNA of a gene that controls transcription of DNA to which it is operatively linked. A portion of the promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated. For use herein, inducible promoters are preferred. The promoters are recognized by an RNA polymerase that is expressed by the host. The RNA polymerase may be endogenous to the host or may be introduced by genetic engineering into the host, either as part of the host chromosome or on an episomal element, including a plasmid containing the DNA encoding the saporin-containing polypeptide. Most preferred promoters for use herein are tightly regulated such that, absent induction, the DNA encoding the saporin-containing protein is not expressed.

As used herein, a transcription terminator region has either (a) a subsegment that encodes a polyadenylation signal and polyadenylation site in the transcript, and/or (b) a subsegment that provides a transcription termination signal that terminates transcription by the polymerase that recognizes the selected promoter. The entire transcription terminator may be obtained from a protein-encoding gene, which may be the same or different from the gene, which is the source of the promoter. Preferred transcription terminator regions are those that are functional in *E. coli*. Transcription terminators are optional components of the expression systems herein, but are employed in preferred embodiments.

As used herein, FGF-mediated pathophysiological condition refers to a deleterious condition characterized by or caused by proliferation of cells that are sensitive to bFGF mitogenic stimulation. Basic FGF-mediated pathophysiological conditions include, but are not limited to, certain tumors, rheumatoid arthritis, restinosis, Dupuytren's Contracture and certain complications of diabetes, such as proliferative retinopathy.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, isolated, substantially pure DNA refers to DNA fragments purified according to standard techniques employed by those skilled in the art (see, e.g., Maniatis et al. (1982) *Molecular Cloning: A Laboratory Manual*, Cold Spring Harbor Laboratory Press, Cold Spring Harbor, N.Y. and Sambrook et al. (1989) *Molecular Cloning: A Laboratory Manual*, Cold Spring Harbor Laboratory Press, Cold Spring Harbor, N.Y.).

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, "culture" means a propagation of cells in a medium conducive to their growth, and all sub-cultures thereof. The term "subculture" refers to a culture of cells grown from cells of another culture (source culture), or any subculture of the source culture, regardless of the number of subculturings that have been performed between the subculture of interest and the source culture.

As used herein, $ID_{50}$ refers to the concentration at which 50% of the cells are killed following a 72-hour incubation with a toxin, such as FGF-SAP.

As used herein, $ED_{50}$ refers to the concentration of saporin-containing protein required to inhibit protein synthesis in treated cells to 50% of the protein synthesis in the absence of the protein DNA constructs DNA constructs provided herein encode a saporin-containing protein, which includes a sequence of nucleotides encoding a saporin polypeptide and an N-terminal extension sequence linked to the amino terminus of the saporin polypeptide.

Preferable saporin polypeptides include polypeptides having substantially the same amino acid sequence and ribosome-inactivating activity as that of saporin-6(SO-6), including the four isoforms, which have heterogeneity at amino acid positions 48 and 91 (see, e.g., Maras et al. (1990) *Biochem. Internat.* 21:631–638 and Barraet al. (1991) *Biotechnol. Appl. Biochem.* 13:48–53. Other suitable saporin polypeptides include other members of the multi-gene family coding for isoforms of saporin-type RIP's including SO-1 and SO-3 (Fordham-Skelton et al. (1990) *Mol. Gen. Genet.* 221:134–138, SO-2 (Fordham-Skelton et al. (1991) *Mol. Gen. Genet.* 229:460–466), SO-4 (Lappi et al. (1985 *Biochem. Biophys. Res. Commun.* 129:934–942) and SO-5 (Montecucchi et al. (1989) *Int. J. Peptide Protein Res.*, 33:263–267).

Presently preferred saporin polypeptides include those having substantially the same amino acid sequence as those listed in SEQ ID NOs 3–7. The isolation and expression of the DNA encoding these proteins is described in Example 1. The most preferred saporin polypeptide is listed in SEQ ID NO 3.

Suitable N-terminal extension regions may be substantially neutral and lack any biological function other than rendering the saporin polypeptide nontoxic or less toxic to the host in which it is expressed. The specific amino acid makeup of the N-terminal extension region does not appear to be critical for rendering the saporin-containing protein nontoxic or less toxic to the host upon expression of the protein.

In a preferred embodiment, the N-terminal extension region is susceptible to cleavage by eukaryotic intracellular proteases, either by general intracellular degradation or by site-specific proteolytic processing of a proteolytic signal sequence such that, upon internalization, the N-terminal extension region of the saporin-containing fusion protein is cleaved or degraded by a cellular eukaryotic protease, which renders the single-fragment saporin protein biologically active, resulting in cell death (see, e.g., European Patent Application EP 0466 222, for a description of suitable site-specific proteolytic signal sequences).

In addition to rendering the saporin polypeptide non-toxic or less toxic to the host cell, suitable N-terminal extension regions may also serve to confer other biological functions to the saporin-containing protein after it has been isolated. In one embodiment, the N-terminal extension region contains a ligand, preferably bFGF, capable of targeting the saporin polypeptide to a specific cell, in vivo and in vitro, whereby saporin-containing protein is internalized and rendered cytotoxic to the targeted cell.

Exemplary ligands include, but are not limited to, those ligands that have previously proven successful in chemical conjugates with saporin such as basic fibroblast growth factor (bFGF), purified human diferric transferrin, and the antigen binding domains of antibodies, Fab fragments (see, e.g., Better et al. (1989) *Meth. Enz.* 178:476–496), such as anti-human immunoglobulin heavy chain monoclonal antibodies and anti-Thy1 monclonal antibodies. Other ligands, include the cell surface binding domains of anti-T lymphocyte monoclonal antibodies, such as, but not limited to, anti-CD5 T-cell surface antigen, anti-CD19 and anti-CD22, anti-CD3, and anti-CD2. Particularly preferred ligands are fibroblast growth factors (FGFs), platelet-derived growth factor (PDGF), vascular endothelial cell growth factor (VEGF), and granulocyte-macrophage colony stimulating factor (GM-CSF). The most preferred ligand is bFGF.

Other ligands may include, but are not limited to, those that have previously proven successful linked to other toxins, such as anti-human transferrin receptor monoclonal antibodies, alpha-melanocyte-stimulating hormone, IL-2, IL-6, transforming growth factor-type alpha (TGF-alpha), and the HIV-binding domain of the human CD4 molecule, and the like.

In preferred embodiments, DNA encoding the saporin polypeptide is linked to DNA encoding an FGF polypeptide. The DNA encoding the FGF polypeptide is modified in order to remove the translation stop codon and other transcriptional or translational stop signals that may be present. The DNA is then ligated to the DNA encoding the saporin polypeptide. The DNA may include a spacer region of one or more codons between the first codon of the saporin and the last codon of the FGF. The size of the spacer region is any length as long as the resulting conjugate exhibits cytotoxic activity upon internalization by a target cell. Presently, spacer regions of from about two to about twelve codons are preferred.

DNA encoding FGFs and/or the amino acid sequences of FGFs are known to those of skill in this art. DNA encoding human acid FGF (Jaye et al. (1986) *Science* 233:541–545), bovine bFGF (Abraham et al. (1986) *Science* 233:545–548), human bFGF (Abraham et al. (1986) *EMBO J.* 5:2523–2528; and Abraham et al. (1986) *Quant. Biol.* 51:657–668) and rat bFGF (see Shimasaki et al. (1988) *Biochem. Biophys. Res. Comm.* and Kurokawa et al. (1988) *Nucleic Acids Res.* 16:5201) are known (see, also, U.S. Pat. No. 5,155,214; U.S. Pat. No. 4,956,455; U.S. Pat. No. 5,026,839; and U.S. Pat. No. 4,994,559). The amino acid sequence of an exemplary mammalian bFGF isolated from bovine pituitary tissue is also known (see, e.g., in Esch et al. (1985) *Proc. Natl. Acad. Sci. USA* 82:6507–6511; and U.S. Pat. No. 4,956,455). The isolated mammalian basic FGF protein is typically a 146-residue polypeptide having a molecular weight of about 16 kD, and a pl of about 9.6; it may be expressed with an amino terminal extension of about 9 residues so that the resulting protein has a molecular weight of about 18 kD.

Plasmids for expression of saporin-containing polypeptides

The DNA construct is introduced into a plasmid for expression in a desired host. In preferred embodiments, the host is a bacterial host. The sequences of nucleotides in the plasmids that are regulatory regions, such as promoters and operators, are operationally associated with one another for transcription of the sequence of nucleotides that encode a saporin-containing protein. The sequence of nucleotides encoding the saporin-containing protein may also include DNA encoding a secretion signal, whereby the resulting peptide is a precursor of saporin. The resulting processed saporin protein, which if not processed such that the resulting protein is identical to a native saporin, retains the cytotoxic activity of the native saporin protein, may be recovered from the periplasmic space or the fermentation medium.

In preferred embodiments the DNA plasmids also include a transcription terminator sequence. The promoter regions and transcription terminators are each independently selected from the same or different genes.

The plasmids used herein preferably include a promoter in operable association with the DNA encoding the saporin-containing protein and are designed for expression of proteins in a bacterial host. It has been found that tightly regulatable promoters are preferred for expression of saporin. Suitable promoters for expression of saporin-containing proteins are widely available and are well known in the art. Inducible promoters or constitutive promoters that are linked to regulatory regions are preferred. Such promoters include, but are not limited to, the T7 phage promoter and other T7-like phage promoters, such as the T3, T5 and SP6 promoters, the trp, lpp, and lac promoters, such as the lacUV5, from *E. coli*; the P10 or polyhedron gene promoter of baculovirus/insect cell expression systems and inducible promoters from other eukaryotic expression systems. For expression of the saporin-containing proteins such promoters are inserted in a plasmid in operative linkage with a control region such as the lac operon.

Preferred promoter regions are those that are inducible and functional in *E. coli*. Examples of suitable inducible promoters and promoter regions include, but are not limited to: the *E. coli* lac operator responsive to isopropyl β-D-thiogalactopyranoside (IPTG; see, et al. Nakamura et al. (1979) *Cell* 18:1109–1117); the metallothionein promoter metal-regulatory-elements responsive to heavy-metal (e.g., zinc) induction (see, e.g., U.S. Pat. No. 4,870,009 to Evans et al.); and the phage T7lac promoter responsive to IPTG (see Studier et al., *Meth. Enzymol.,* 185: 60–89, 1990; and U.S. Pat. No. 4,952,496).

The plasmids also preferably include a selectable marker gene or genes that are functional in the host. A selectable marker gene includes any gene that confers a phenotype on bacteria that allows transformed bacterial cells to be identified and selectively grown from among a vast majority of untransformed cells. Suitable selectable marker genes for bacterial hosts, for example, include the ampicillin resistance gene (Amp$^r$), tetracycline resistance gene (Tc$^r$) and the kanamycin resistance gene (Kan$^r$). The kanamycin resistance gene is presently preferred.

The preferred plasmids also include DNA encoding a signal for secretion of the operably saporin-containing protein. Secretion signals suitable for use are widely available and are well known in the art. Prokaryotic and eukaryotic secretion signals functional in *E. coli* may be employed. The presently preferred secretion signals include, but are not limited to, those encoded by the following *E. coli* genes: ompA, ompT, ompF, ompC, beta-lactamase, and alkaline phosphatase, and the like (von Heijne (1985) *J. Mol. Biol.* 184:99–105). In addition, the bacterial pelB gene secretion signal (Lei et al. (1987) *J. Bacteriol.* 169:4379, 1987), the phoA secretion signal, and the cek2 functional in insect cell may be employed. The most preferred secretion signal is the *E. coli* ompA secretion signal. Other prokaryotic and eukaryotic secretion signals known to those of skill in the art may also be employed (see, e.g., von Heijne (1985) *J. Mol. Biol.* 184:99–105). Using the methods described herein, one of skill in the art can substitute secretion signals that are functional in either yeast, insect or mammalian cells to secrete saporin-containing proteins from those cells.

Particularly preferred plasmids for transformation of *E. coli* cells include the pET expression vectors (see, U.S. Pat. No. 4,952,496; available from NOVAGEN, Madison, Wis.). Such plasmids include pET 11a, which contains the T7lac promoter, T7 terminator, the inducible *E. coli* lac operator, and the lac repressor gene; and pET 12a–c, which contain the T7 promoter, T7 terminator, and the *E. coli* ompT secretion signal.

Other preferred plasmids include the pIN-IIIompA plasmids (see, U.S. Pat. No. 4,575,013 to Inouye; see, also, Duffaud et al. (1987) *Meth. Enz.* 153:492–507), such as pIN-IIIompA2. The pIN-IIIompA plasmids include an insertion site for the heterologous DNA (the DNA encoding a saporin-containing protein) linked for transcriptional expression in reading phase with four functional fragments derived from the lipoprotein gene of E. coli. The plasmids also include a DNA fragment coding for the signal peptide of the ompA protein of E. coli, positioned such that the desired polypeptide is expressed with the ompA signal peptide at its amino terminus, thereby allowing efficient secretion across the cytoplasmic membrane. The plasmids further include DNA encoding a specific segment of the E. coli lac promoter-operator, which is positioned in the proper orientation for transcriptional expression of the desired polypeptide, as well as a separate functional E. coli lacI gene encoding the associated repressor molecule that, in the absence of lac operon inducer, interacts with the lac promoter-operator to prevent transcription therefrom. Expression of the desired polypeptide is under the control of the lipoprotein (Ipp) promoter and the lac promoter-operator, although transcription from either promoter is normally blocked by the repressor molecule. The repressor is selectively inactivated by means of an inducer molecule thereby inducing transcriptional expression of the desired polypeptide from both promoters.

As described above, a preferred embodiment calls for the incorporation of a bFGF ligand within the N-terminal extension region of the fusion protein. The most preferred bFGF coding region is set forth in SEQ ID NO 12, nucleotides 1–465. Another preferred coding region is set forth in SEQ ID NO 13, nucleotides 1–465. In addition to basic FGF (bFGF) and acidic FGF(aFGF), there are known to be a number of other proteins exhibiting basic FGF mitogenic activity mediated through binding to an FGF receptor. Other FGF proteins in addition to aFGF include HST, INT/2, FGF-5, FGF-6, KGF(FGF-7), FGF-8, and FGF-9 (see, e.g., Baird et al. (1989) *Brit. Med. Bull* 45:438–452; Tanaka et al. (1992) *Proc. Natl. Acad. Sci. USA* 89:8928–8932). All of the FGF proteins induce mitogenic activity in a wide variety of normal diploid mesoderm-derived and neural crest-derived cells. A test of such "FGF mitogenic activity" is the ability to stimulate proliferation of cultured bovine aortic endothelial cells, as described in Gospodarowicz et al. (1982) *J. Biol. Chem.*, 257, 12266–12278 Gospodarowicz et al. (1976) *Proc. Natl. Acad. Sci. USA* 73:4120–4124.

In a preferred embodiment, the DNA fragment is replicated in bacterial cells, preferably in E. coli. The preferred DNA fragment also includes a bacterial origin of replication, to ensure the maintenance of the DNA fragment from generation to generation of the bacteria. In this way, large quantities of the DNA fragment can be produced by replication in bacteria. Preferred bacterial origins of replication include, but are not limited to, the f1-ori and col E1 origins of replication. Preferred hosts contain chromosomal copies of DNA encoding T7 RNA polymerase operably linked to an inducible promoter, such as the lacUV promoter (see, U.S. Pat. No. 4,952,496). Such hosts include, but are not limited to, lysogens E. coli strains HMS174(DE3)pLysS, BL21 (DE3)pLysS, HMS174(DE3) and BL21(DE3). Strain BL21 (DE3) is preferred. The pLys strains provide low levels of T7 lysozyme, a natural inhibitor of T7 RNA polymerase.

The DNA fragments provided optionally further contain a gene coding for a repressor-protein. The repressor-protein is capable of repressing the transcription of a promoter that contains sequences of nucleotides to which the repressor-protein binds. The promoter can be derepressed by altering the physiological conditions of the cell. The alteration can be accomplished by the addition to the growth medium of a molecule that inhibits, for example, the ability to interact with the operator or with regulatory proteins or other regions of the DNA or by altering the temperature of the growth media. Preferred repressor-proteins include, but are not limited to the E. coli. lacI repressor responsive to IPTG induction, the temperature sensitive cI857 repressor, and the like. The E. coli lacI repressor is preferred.

The resulting bFGF-fusion proteins are highly cytotoxic when internalized by targeted cells.

Host cells for expression of saporin-containing polypeptides

Host organisms include those organisms in which recombinant production of heterologous proteins have been carried out, such as, but not limited to, bacteria (for example, *E. coli*), yeast (for example, *Saccharomyces cerevisiae* and *Pichia pastoris*), mammalian cells, insect cells. Presently preferred host organisms are strains of bacteria. Most preferred host organisms are strains of *E. coli.*

Methods for Recombinant SAP production

The DNA encoding saporin-containing protein is introduced into a plasmid in operative linkage to an appropriate promoter for expression of polypeptides in a selected host organism. The DNA fragment encoding the biologically active saporin polypeptide may also include a protein secretion signal that functions in the selected host to direct the mature polypeptide into the periplasm or culture medium. The resulting saporin-containing protein can be purified by methods routinely used in the art, including, methods described hereinafter in the Examples.

Methods of transforming suitable host cells, preferably bacterial cells, and more preferably *E. coli* cells, as well as methods applicable for culturing said cells containing a gene encoding a heterologous protein, are generally known in the art. See, for example, Sambrook et al. (1989) *Molecular Cloning: A Laboratory Manual*, Cold Spring Harbor Laboratory Press, Cold Spring Harbor, N.Y.

The DNA construct encoding the saporin-containing protein is introduced into the host cell by any suitable means, including, but not limited to transformation employing plasmids, viral, or bacterial phage vectors, transfection, electroporation, lipofection, and the like. The heterologous DNA can optionally include sequences, such as origins of replication that allow for the extrachromosomal maintenance of the saporin-containing plasmid, or can be designed to integrate into the genome of the host (as an alternative means to ensure stable maintenance in the host).

Positive transformants can be characterized by Southern blot analysis (Sambrook et al. (1989) *Molecular Cloning: A Laboratory Manual*, Cold Spring Harbor Laboratory Press, Cold Spring Harbor, N.Y.) for the site of DNA integration; Northern blots for inducible-promoter-responsive saporin gene expression; and product analysis for the presence of saporin-containing proteins in either the cytoplasm, periplasm, or the growth media.

Once the saporin-containing DNA fragment has been introduced into the host cell, the desired saporin-containing protein is produced by subjecting the host cell to conditions under which the promoter is induced, whereby the operatively linked DNA is transcribed. In a preferred embodiment, such conditions are those that induce expression from the *E. coli* lac operon. The plasmid containing the DNA encoding the saporin-containing protein also includes the lac operator (O) region within the promoter and may also include the lac I gene encoding the lac repressor protein (see, e.g., Muller-Hill et al. (1968) *Proc. Natl. Acad. Sci. USA* 59:1259–12649). The lac repressor represses the expression from the lac promoter until induced by the addition of IPTG in an amount sufficient to induce transcription of the DNA encoding the saporin-containing protein.

The expression of saporin in *E. coli* is, thus accomplished in a two-stage process. In the first stage, a culture of transformed *E. coli* cells is grown under conditions in which the expression of the saporin-containing protein within the transforming plasmid, preferably pOMPAG4, is repressed by virtue of the lac repressor. In this stage cell density increases. When an optimum density is reached, the second stage commences by addition of IPTG, which prevents binding of repressor to the operator thereby inducing the lac promoter and transcription of the saporin-encoding DNA.

In a preferred embodiment, the promoter is the T7 RNA polymerase promoter, which may be linked to the lac operator and the *E. coli* host strain includes DNA encoding T7 RNA polymerase operably linked to the lac operator and a promoter, preferably the lacUV5 promoter. Addition of IPTG induces expression of the T7 RNA polymerase and the T7 promoter, which is recognized by the T7 RNA polymerase. In more preferred embodiments, the DNA construct includes a transcription terminator that is recognized by T7 RNA polymerase.

Transformed strains, which are of the desired phenotype and genotype, are grown in fermentors by suitable methods well known in the art. In the first, or growth stage, expression hosts are cultured in defined minimal medium lacking the inducing condition, preferably IPTG. When grown in such conditions, heterologous gene expression is completely repressed, which allows the generation of cell mass in the absence of heterologous protein expression. Subsequent to the period of growth under repression of heterologous gene expression, the inducer, preferably IPTG, is added to the fermentation broth, thereby inducing expression of any DNA operatively linked to an IPTG-responsive promoter (a promoter region that contains lac operator). This last stage is the induction stage.

In a preferred embodiment, the expressed saporin-containing protein is isolated from either the cytoplasm, periplasm, or the cell culture media. More preferably, the expressed saporin-containing protein is isolated as a secreted entity from either the periplasm or the culture medium. Most preferred, is the isolation of the saporin containing product from the periplasm.

The resulting saporin-containing protein can be suitably isolated from the other fermentation products by methods routinely used in the art, e.g., using a suitable affinity column as described in Example 1.E–F and 2.D; precipitation with ammonium sulfate; gel filtration; chromatography, preparative flat-bed iso-electric focusing; gel electrophoresis, high performance liquid chromatography (HPLC); and the like. Methods of isolating saporin are described in Lappi et al., *Biochem. Biophys. Res. Commun.,* 129:934–942.

In practicing the methods herein, an EcoR I fragment encoding the entire mature SAP polypeptide and fifteen amino acids of the saporin signal sequence has been inserted into the periplasmic secretion vector pIN-IIIompA2 such that the DNA encoding the saporin signal sequence and saporin protein was operatively linked to the DNA encoding the ompA leader to produce plasmid pOMPAG4, which was introduced in *E. coli* host cells. Upon induction of expression of the DNA encoding saporin-containing protein, saporin-containing polypeptide was isolated from the periplasm and cytoplasm. The saporin-containing polypeptide has been purified by immunoaffinity chromatography. Amino acid sequence analysis of the periplasmic protein indicated that the ompA signal was properly processed and that from three to ten amino acids of the native signal sequence were also removed. Similar analysis of the cytoplasmic protein indicated that the entire native signal peptide and an additional two amino acids were removed.

DNA encoding full-length bFGF has been linked to DNA encoding the mature saporin protein and introduced into the pET vectors, pET-11a and pET-12a expression vectors (NOVAGEN, Madison, Wis.), for intracellular and periplasmic expression, respectively, of FGF-SAP fusion proteins. The resulting fusion proteins exhibit cytotoxic activity and appear to be at least as potent as the chemically conjugated FGF-SAP preparations.

The following examples are included for illustrative purposes only and are not intended to limit the scope of the invention.

EXAMPLE 1

RECOMBINANT PRODUCTION OF SAPORIN-CONTAINING PROTEIN

A. General Descriptions

1. Bacterial Strains

*E. coli* strain JA221 (Ipp$^-$ hdsM+trpE5 leuB6 lacY recA1 F'[laCI$^q$ lac$^+$ pro$^+$]) is publicly available from the American Type Culture Collection (ATCC), Rockville, Md. 20852, under the accession number ATCC 33875. (JA221 is also available from the Northern Regional Research Center (NRRL), Agricultural Research Service, U.S. Department of Agriculture, Peoria, Ill. 61604, under the accession number NRRL B-15211; see, also, U.S. Pat. No. 4,757,013 to Inouye; and Nakamura et al. (1979) *Cell* 18:1109–1117). Strain INV1$\alpha$ is commercially available from Invitrogen, San Diego, Calif.

2. DNA Manipulations

The restriction and modification enzymes employed herein are commercially available in the U.S. Native saporin and rabbit polyclonal antiserum to saporin were obtained as previously described in Lappi et al. *Biochem. Biophys. Res. Comm.,* 129: 934–942. Ricin A chain is commercially available from SIGMA, Milwaukee, Wis. Antiserum was linked to Affi-gel 10 (BIO-RAD, Emeryville, Calif.) according to the manufacturer's instructions. The sequencing of the different constructions was done using the Sequenase kit of United States Biochemical Corporation (version 2.0) according to the manufacturer's instructions. Minipreparation and maxipreparations of plasmids, preparation of competent cells, transformation, M13 manipulation, bacterial media, Western blotting, and ELISA assays were according to Sambrook et al. (J. Sambrook, E. F. Fritsch and T. Maniatis. (1989) *Molecular Cloning: A Laboratory Manual*, Cold Spring Harbor Laboratory Press, Cold Spring Harbor, N.Y.). The purification of DNA fragments was done using the Geneclean II kit (Bio 101) according to the manufacturer's instructions. SDS gel electrophoresis was performed on a Phastsystem (Pharmacia).

Western blotting was accomplished by transfer of the electrophoresed protein to nitrocellulose using the PhastTransfer system, as described by the manufacturer. The antiserum to SAP was used at a dilution of 1:1000. Horseradish peroxidase labelled anti-lgG was used as the second antibody (see Davis et al. (1986) *Basic methods in molecular biology*, New York, Elsevier Science Publishing Co., pp 1–338).

B. Isolation of DNA encoding saporin

1. Isolation of Genomic DNA and Preparation of Polymerase Chain Reaction (PCR) Primers

*Saponaria officinalis* leaf genomic DNA was prepared as described in Bianchi et al. (1988) *Plant Mol. Biol.*

11:203–214. Primers for genomic DNA amplifications were synthesized in a 380B automatic DNA synthesizer. The primer corresponding to the "sense" strand of saporin (SEQ ID NO 1) includes an EcoR I restriction site adapter immediately upstream of the DNA codon for amino acid-15 of the native saporin N-terminal leader sequence (SEQ ID NO 1):

5'-CTGCAGAATTCGCATGGATCCTGCTTCAAT-3'.

The primer corresponding to the "antisense" strand of saporin (SEQ ID NO 2) complements the coding sequence of saporin starting from the last 5 nucleotides of the DNA encoding the carboxyl end of the mature peptide, introduces a translation stop codon after the sequence encoding mature saporin and introduces an EcoR I restriction site downstream of the saporin-encoding DNA and the introduced stop codon (SEQ ID NO 2):
5'-CTGCAGAATTCGCCTCGTTTGACTAC TTTG-3'.

2. PCR to Amplify DNA Encoding Saporin

Unfractionated *Saponaria officinalis* leaf genomic DNA (1 μl) was mixed in a final volume of 100 μl containing 10 mM Tri-HCl (pH 8.3), 50 mM KCl, 0.01% gelatin, 2 mM $MgCl_2$, 0.2 mM dNTPs, 0.8 μg of each primer. Next, 2.5 U TaqI DNA polymerase (Perkin Elmer Cetus) was added and the mixture was overlaid with 30 μl of mineral oil (Sigma). Incubations were done in a DNA Thermal Cycler (Perkin Elmer Cetus). One cycle included a denaturation step (94° C. for 1 min.), an annealing step (60° C. for 2 min.), and an elongation step (72° C. for 3 min.). After 30 cycles, a 10 μl aliquot of each reaction was run on a 1.5% agarose gel to verify the correct structure of the amplified product.

The amplified DNA was digested with EcoR I and subcloned into EcoR I-restricted M13mp18 (NEW ENGLAND BIOLABS, Beverly, Mass.; see, also, Yanisch-Perron et al. (1985), "Improved M13 phage cloning vectors and host strains: Nucleotide sequences of the M13mp18 and pUC19 vectors", *Gene* 33:103). Single-stranded DNA from recombinant phages was sequenced using oligonucleotides based on internal points in the coding sequence of saporin (see, Bennati et al. (1989) *Eur. J. Biochem.* 183:465–470). Nine of the M13mp18 derivatives were sequenced and compared. Of the nine sequenced clones, five had unique sequences, set forth as SEQ ID NOs 3–7, respectively. The clones were designated M13mp18-G4, -G1, -G2, -G7, and -G9. Each of these clones contains all of the saporin coding sequence and 45 nucleotides of DNA encoding the native saporin N-terminal leader peptide.

C. pOMPAG4 Plasmid Construction

M13 mp18-G4, containing the SEQ ID NO 3 clone from Example 1.B.2., was digested with EcoR I, and the resulting fragment was ligated into the EcoR I site of the vector pIN-IIIompA2 (see, e.g., see, U.S. Pat. No. 4,575,013 to Inouye; and Duffaud et al. (1987) *Meth. Enz.* 153:492–507) using the methods described in Example 1.A.2. The ligation was accomplished such that the DNA encoding saporin, including the N-terminal extension, was fused to the leader peptide segment of the bacterial ompA gene. The resulting plasmid pOMPAG4 contains the Ipp promoter [Nakamura, K. and Inouye, M. *Cell.*, 18:1109–1117 (1979)], the *E. coli* lac promoter operator sequence (lac O) and the *E. coli* ompA gene secretion signal in operative association with each other and with the saporin and native N-terminal leader-encoding DNA listed in SEQ ID NO 3. The plasmid also includes the *E. coli* lac repressor gene (lac I).

The M13 mp18-G1, -G2, -G7, and -G9 clones obtained from Example 1.B.2, containing SEQ ID NOs 4–7 respectively, are digested with EcoR I and ligated into EcoR I digested pIN-IIIompA2 as described for M13 mp18-G4 above in this example. The resulting plasmids, labeled pOMPAG1, pOMPAG2, pOMPAG7, pOMPA9, are screened, expressed, purified, and characterized as described for the plasmid pOMPAG4.

INV1 α competent cells were transformed with pOMPAG4 and cultures containing the desired plasmid structure were grown further in order to obtain a large preparation of isolated pOMPAG4 plasmid using methods described in Example 1.A.2.

D. Saporin expression in *E. coli*

The pOMPAG4 transformed *E. coli* cells were grown under conditions in which the expression of the saporin-containing protein is repressed by the lac repressor to an O.D. in or at the end of the log phase of growth after which IPTG was added to induce expression of the saporin-encoding DNA.

To generate a large-batch culture of pOMPAG4 transformed *E. coli* cells, an overnight culture (lasting approximately 16 hours) of JA221 *E. coli* cells transformed with the plasmid pOMPAG4 in LB broth (see eg., Sambrook et al. (1989) *Molecular Cloning: A Laboratory Manual*, Cold Spring Harbor Laboratory Press, Cold Spring Harbor, N.Y.) containing 125 mg/ml ampicillin was diluted 1:100 into a flask containing 750 ml LB broth with 125 mg/ml ampicillin. Cells were grown at logarithmic phase shaking at 37° C. until the optical density at 550 nm reached 0.9 measured in a spectrophotometer.

In the second step, saporin expression was induced by the addition of IPTG (Sigma) to a final concentration of 0.2 mM. Induced cultures were grown for 2 additional hours and then harvested by centrifugation (25 min., 6500×g). The cell pellet was resuspended in ice cold 1.0M TRIS, pH 9.0, 2 mM EDTA (10 ml were added to each gram of pellet). The resuspended material was kept on ice for 20–60 minutes and then centrifuged (20 min., 6500×g) to separate the periplasmic fraction of *E. coli*, which corresponds to the supernatant, from the intracellular fraction corresponding to the pellet.

E. Purification of recombinant Saporin secreted to periplasm

1. Anti-SAP Immuno-Affinity Purification

The periplasmic fraction from Example 1.D. was dialyzed against borate-buffered saline (BBS: 5 mM boric acid, 1.25 mM borax, 145 mM sodium chloride, pH 8.5). The dialysate was loaded onto an immunoaffinity column (0.5×2 cm) of anti-saporin antibodies, obtained as described in Lappi et al., *Biochem. Biophys. Res. Comm.*, 129: 934–942 (1985), bound to Affi-gel 10 and equilibrated in BBS at a flow rate of about 0.5 ml/min. The column was washed with BBS until the absorbance at 280 nm of the flow-through was reduced to baseline. Next the column containing the antibody bound saporin was eluted with 1.0M acetic acid and 0.5 ml fractions were collected in tubes containing 0.3 ml of 2M ammonium hydroxide, pH 10. The fractions were analyzed by ELISA (see, e.g., Sambrook et al. (1989) *Molecular Cloning: A Laboratory Manual*, Cold Spring Harbor Laboratory Press, Cold Spring Harbor, N.Y.). The peak fraction of the ELISA was analyzed by Western blotting as described in Example 1.A.2 and showed a single band with a slightly higher molecular weight than native saporin. The fractions that contained saporin protein, as determined by the ELISA, were then pooled for further purification.

2. Reverse Phase High Performance Liquid Chromatography Purification

To further purify the saporin secreted into the periplasm, the pooled fractions from Example 1.E.1. were diluted 1:1 with 0.1% trifluoroacetic acid (TFA) in water and chromatographed in reverse phase high pressure liquid chromatography (HPLC) on a Vydac C4 column (Western Analytical) equilibrated in 20% acetonitrile, 0.1% TFA in water. The protein was eluted with a 20 minute gradient to 60% acetonitrile. The HPLC produced a single peak that was the only area of immunoreactivity with anti-SAP antiserum when analyzed by a western blot as described in Example 1.E.1. Samples were assayed by the ELISA. Sequence analysis was performed by Edman degradation in a gas-phase sequenator (Applied Biosystems) as described in Lappi et al., *Biochem. Biophys. Res. Comm.*, 129: 934–942 (1985). The results indicated that five polypeptides were obtained that differ in the length, between 7 and 12 amino acids, of the N-terminal saporin leader before the initial amino acid valine of the mature native saporin (SEQ ID NO 3: residue-12 through-7). All of the N-terminal extended variants retained cytotoxic activity. The size of the native lader is 18 residues, indicating that the native signal peptide is not properly processed by bacterial processing enzymes. The ompA signal was, however, properly processed.

F. Purification of intracellular soluble saporin

To purify the cytosolic soluble saporin protein, the pellet from the intracellular fraction of Example 1.E. above was resuspended in lysis buffer (30 mM TRIS, 2 mM EDTA, 0.1% Triton X-100, pH 8.0, with 1 mM PMSF, 10 µg/ml pepstatin A, 10 µg aprotinin, µg/ml leupeptin and 100 µg/ml lysozyme, 3.5 ml per gram of original pellet). To lyse the cells, the suspension was left at room temperature for one hour, then frozen in liquid nitrogen and thawed in a 37° C. bath three times, and then sonicated for two minutes. The lysate was centrifuged at 11,500×g for 30 min. The supernatant was removed and stored. The pellet was resuspended in an equal volume of lysis buffer, centrifuged as before, and this second supernatant was combined with the first. The pooled supernatants were dialyzed versus BBS and chromatographed over the immunoaffinity column as described in Example 1.E.1. This material also retained cytotoxic activity.

G. Assay for cytotoxic activity

The RIP activity of recombinant saporin was compared to the RIP activity of native SAP in an in vitro assay measuring cell-free protein synthesis in a nuclease-treated rabbit reticulocyte lysate (Promega). Samples of immunoaffinity-purified saporin, obtained in Example 1.E.1., were diluted in PBS and 5 µl of sample was added on ice to 35 µl of rabbit reticulocyte lysate and 10 µl of a reaction mixture containing 0.5 µl of Brome Mosaic Virus RNA, 1 mM amino acid mixture minus leucine, 5, µCi of tritiated leucine and 3 µl of water. Assay tubes were incubated 1 hour in a 30  C. water bath. The reaction was stopped by transferring the tubes to ice and adding 5 µl of the assay mixture, in triplicate, to 75 µl of 1N sodium hydroxide, 2.5% hydrogen peroxide in the wells of a Milliliter HA 96-well filtration plate (Millipore). When the red color had bleached from the samples, 300 µl of ice cold 25% trichloroacetic acid (TCA) were added to each well and the plate left on ice for another 30 min. Vacuum filtration was performed with a Millipore vacuum holder. The wells were washed three times with 300 µl of ice cold 8% TCA. After drying, the filter paper circles were punched out of the 96-well plate and counted by liquid scintillation techniques.

The $IC_{50}$ for the recombinant and native saporin were approximately 20 pM. Therefore, recombinant saporin-containing protein has full protein synthesis inhibition activity when compared to native saporin.

EXAMPLE 2

Recombinant Production of FGF-SAP Fusion Protein

A. General Descriptions

1. Bacterial Strains and Plasmids

*E. coli* strains BL21(DE3), BL21(DE3)pLysS, HMS174 (DE3) and HMS174(DE3)pLysS were purchased from NOVAGEN, Madison, Wis. Plasmid pFC80, described below, has been described in the WIPO International Patent Application No. WO 90/02800, except that the bFGF coding sequence in the plasmid designated pFC80 herein has the sequence set forth as SEQ ID NO 12, nucleotides 1–465. The plasmids described herein may be prepared using pFC80 as a starting material or, alternatively, by starting with a fragment containg the CII ribosome binding site (SEQ ID NO 15) linked to the FGF-encoding DNA (SEQ ID NO 12).

2. DNA Manipulations

The restriction and modification enzymes employed here are commercially available in the U.S. Native SAP, chemically conjugated bFGF-SAP and rabbit polyclonal antiserum to SAP and FGF were obtained as described in Lappi et al., *Biochem. Biophys. Res. Comm.*, 129: 934–942 (1985) and Lappi et al., *Biochem. Biophys. Res. Comm.*, 160: 917–923 (1989). The pET System Induction Control was purchased from NOVAGEN, Madison, Wis. The sequencing of the different constructions was done using the Sequenase kit of United States Biochemical Corporation (version 2.0). Minipreparation and maxipreparations of plasmids, preparation of competent cells, transformation, M13 manipulation, bacterial media and Western blotting were performed using routine methods (see, e.g.,. Sambrook et al. (1989) *Molecular Cloning: A Laboratory Manual*, Cold Spring Harbor Laboratory Press, Cold Spring Harbor, N.Y.). The purification of DNA fragments was done using the Geneclean II kit, purchased from Bio 101. SDS gel electrophoresis was performed on a Phastsystem (Pharmacia).

B. Construction of plasmids encoding FGF-SAP fusion proteins

1. Construction of FGFM13 That Contains DNA Encoding the CI Ribosome Binding Site Linked to FGF A Nco I restriction site was introduced into the SAP-encoding DNA the M13mp18-G4 clone, prepared as described in Example 1.B.2. by site-directed mutagenesis method using the Amersham In vitro-mutagenesis system 2.1. The oligonucleotide employed to create the Nco I restriction site was synthesized using a 380B automatic DNA synthesizer (Applied Biosystems) and is listed as:

SEQ ID NO 8-CAACAACTGCCATGGTCACATC.

This oligonucleotide containing the Nco I site replaced the original SAP-containing coding sequence at SEQ ID NO 3, nts 32–53. The resulting M13mp18-G4 derivative is termed mpNG4.

In order to produce a bFGF coding sequence in which the stop codon was removed, the FGF-encoding DNA was subcloned into a M13 phage and subjected to site-directed mutagenesis. Plasmid pFC80 is a derivative of pDS20 (see, e.g., Duester et al. (1982) *Cell* 30:855–864; see also U.S. Pat. Nos. 4,914,027, 5,037,744, 5,100,784, and 5,187,261; see, also, PCT Internationl Application No. WO 90/02800; and European Patent Application No. EP 267703 A1), which is almost the same as plasmid pKG1800 (see, Bernardi et al. (1990) *DNA Sequence* 1:147–150; see, also McKenney et al. (1981) pp. 383–415 in *Gene Amplification and Analysis* 2: *Analysis of Nucleic Acids by Enzymatic Methods* Chirikjian et al., eds, North Holland Publishing Company, Amsterdam) except that it contains an extra 440 bp at the distal end of galk between nucleotides 2440 and 2880 in pDS20. Plasmid pKG1800 includes the 2880 bp EcoR I-Pvu II of pBR322 that contains the contains the amplicillin resistance gene and an origin of replication.

Plasmid pFC80 was prepared from pDS20 by replacing the entire galK gene with the FGF-encoding DNA of SEQ ID NO. 12, inserting the trp promoter (SEQ ID NO. 14) and the bacteriophage lambda CII ribosome binding site (SEQ. ID No. 15; see, e.g., Schwarz et al. (1978) *Nature* 272:410) upstream of and operatively linked to the FGF-encoding DNA. The Trp promoter can be obtained from plasmid pDR720 (Pharmacia PL Biochemicals) or sythesized according to SEQ ID NO. 14. Plasmid pFC80, contains the 2880 bp EcoR I-BamH I fragment of plasmid pSD20, a synthetic Sal I-Nde I fragment that encodes the Trp promoter region (SEQ ID NO. 14):

<u>EcoR I</u>
AATTCCCCTGTTGACAATTAATCATCGAACTAGTTAACTAGTACGCAGCTTGGCTGCAG and the CII ribosome binding site (SEQ ID NO.15)):

<u>Sal I</u>                                              <u>Nde I</u>
GTCGACCAAGCTTGGGCATACATTCAATCAATTGTTATCTAAGGAAATACTTACATATG

The FGF-encoding DNA was removed from pFC80 by treating it as follows. The pFC80 plasmid was digested by Hga I and Sal I, which produces a fragment containg the CII ribosome binding site linked to the FGF-encoding DNA. The resulting fragment was blunt ended with Klenow's reagent and inserted into M13mp18 that had been opened by Sma I and treated with alkaline phosphatase for blunt-end ligation. In order to remove the stop codon, an insert in the ORI minus direction was mutagenized using the Amersham kit, as described above, using the following oligonucleotide (SEQ ID NO 9): GCTAAGAGCGCCATGGAGA. SEQ ID NO 9 contains 1 nucleotide between the FGF carboxy terminal serine codon and a Nco I restriction site, and it replaced the following wild type FGF encoding DNA having SEQ ID NO 10:

GCT AAG AGC TGA  CCA TGG AGA.
Ala Lys Ser STOP Pro Trp Arg

The resulting mutant derivative of M13mp18, lacking a native stop codon after the carboxy terminal serine codon of bFGF, was designated FGFM13. The mutagenized region of FGFM13 contained the correct sequence (SEQ ID NO 11).

2. Preparation of Plasmids pFS92 (PZ1A), PZ1B and PZ1C That Encode the FGF-SAP Fusion Protein a. Plasmid pFS92 (Also Designated PZ1A)

Plasmid FGFM13 was cut with Nco I and Sac I to yield a fragment containing the CII ribosome binding site linked to the bFGF coding sequence with the stop codon replaced.

The M13mp18 derivative mpNG4 containing the saporin coding sequence was also cut with restriction endonucleases Nco I and Sac I, and the bFGF coding fragment from FGFM13 was inserted by ligation to DNA encoding the fusion protein bFGF-SAP into the M13mp18 derivative to produce mpFGF-SAP, which contains the CII ribosome binding site linked to the FGF-SAP fusion gene. The sequence of the fusion gene is set forth in SEQ ID NO 12 and indicates that the FGF protein carboxy terminus and the saporin protein amino terminus are separated by 6 nucleotides (SEQ ID NOs 12 and 13, ntds 466–471) that encode two amino acids Ala Met.

Plasmid mpFGF-SAP was digested with Xba I and EcoR I and the resulting fragment containing the bFGF-SAP coding sequence was isolated and ligated into plasmid pET-11a (available from NOVAGEN, Madison, Wis.; for a description of the plasmids see U.S. Pat. No. 4,952,496; see, also Studier et al. (1990) *Meth. Enz.* 185:60–89; Studier et al. (1986) *J. Mol. Biol.* 189:113–130; Rosenberg et al. (1987) *Gene* 56:125–135)that had also been treated with EcoR I and Xba I. The resulting plasmid was designated pFS92. It was renamed PZ1A.

Plasmid pFS92 (or PZ1A) contains DNA the entire basic FGF protein (SEQ ID NO 12), a 2-amino acid long connecting peptide, and amino acids 1 to 253 of the mature SAP protein. Plasmid pFS92 also includes the CII ribosome binding site linked to the FGF-SAP fusion protein and the T7 promoter region from pET-11a.

*E. coli* strain BL21(DE3)pLysS (NOVAGEN, Madison Wis.) was transfomed with pFS92 according to manufacturer's instructions and the methods described in Example 2.A.2.

b. Plasmid PZ1B

Plasmid pFS92 was digested with EcoR I, the ends repaired by adding nucleoside triphosphates and Klenow DNA polymerase, and then digested with Nde I to release the FGF-encoding DNA without the CII ribosome binding site. This fragment was ligated into pET 11a, which had been BamH I digested, treated to repair the ends, and digested with Nde I. The resulting plasmid was designated PZ1B. PZ1B includes the T7 transcription terminator and the pET-11a ribosome binding site.

*E. coli* strain BL21 (DE3) (NOVAGEN, Madison Wis.) was transfomed with PZ1B according to manufacturer's instructions and the methods described in Example 2.A.2.

c. Plasmid PZ1C

Plasmid PZ1C was prepared from PZ1B by replacing the amplicillin resistance gene with a kanamycin resistance gene.

c. Plasmid PZ1D

Plasmid pFS92 was digested with EcoR I and Nde I to release the FGF-encoding DNA without the CII ribosome binding site and the and the ends were repaired. This fragment was ligated into pET 12a, which had been BamH I digested and treated to repair the ends. The resulting plasmid was designated PZ1D. PZ1D includes DNA encoding the OMP T secretion signal operatively linked to DNA encoding the fusion protein.

E. coli strains BL21(DE3), BL21(DE3)pLysS, HMS174 (DE3) and HMS174(DE3)pLysS (NOVAGEN, Madison Wis.) were transfomed with PZ1D according to manufacturer's instructions and the methods described in Example 2.A.2.

C. Expression of the recombinant bFGF-SAP fusion proteins

The two-stage method described above was used to produce recombinant bFGF-SAP protein (hereinafter bFGF-SAP fusion protein).

1. Expression of rbFGF-SAP from pFS92 (PZ1A)

Three liters of LB broth containing ampicillin (50 µg/ml) and chloramphenicol (25 µg/ml) were inoculated with pFS92 plasmid-containing bacterial cells (strain BL21 (DE3)pLysS) from an overnight culture (1:100 dilution) that were obtained according to Example 2.B. Cells were grown at 37° C. in an incubator shaker to an $OD_{600}$ of 0.7. IPTG (Sigma Chemical, St. Louis, Mo.) was added to a final concentration of 0.2 mM and growth was continued for 1.5 hours at which time cells were centrifuged.

Subsequent experiments have shown that growing the BL21(DE3)pLysS cells at 30° C. instead of 37° C. improves yields. When the cells are grown at 30° C. they are grown to an $OD_{600}$ of 1.5 prior to induction. Following induction, growth is continued for about 2 to 2.5 hours at which time the cells are harvested by centrifugation.

The pellet was resuspended in lysis solution (45–60 ml per 16 g of pellet; 20 mM TRIS, pH 7.4, 5 mM EDTA, 10% sucrose, 150 mM NaCl, lysozyme, 100 µg/ml, aprotinin, 10 µg/ml, leupeptin, 10 µg/ml, pepstatin A, 10 µg/ml and 1 mM PMSF) and incubated with stirring for 1 hour at room temperature. The solution was frozen and thawed three times and sonicated for 2.5 minutes. The suspension was centrifuged at 12,000×g for 1 hour; the resulting first-supernatant was saved and the pellet was resuspended in another volume of lysis solution without lysozyme. The resuspended material was centrifuged again to produce a second-supernatant, and the two supernatants were pooled and dialyzed against borate buffered saline, pH 8.3.

2. Expression of bFGF-SAP Fusion Protein from PZ1B and PZ1C

Two hundred and fifty mls. of LB medium containing ampicillin (100 µg/ml) were inoculated with a fresh glycerol stock of PZ1B. Cells were grown at 30° C. in an incubator shaker to an $OD_{600}$ of 0.7 and stored overnight at 4° C. The following day the cells were pelleted and resuspended in fresh LB medium (no ampicillin). The cells were divided into 5 1-liter batches and grown at 30° C. in an incubator shaker to an $OD_{600}$ of 1.5. iPTG (SIGMA CHEMICAL, St. Louis, Mo.) was added to a final concentration of 0.1 mM and growth was continued for about 2 to 2.5 hours at which time cells were harvested by centrifugation.

In order to grow PZ1C, prior to induction, the cells are grown in meidum containing kanamycin (50 µg/ml) in place of ampicillin.

3. Expression of bFGF-SAP Fusion Protein from PZ1D

Two hundred and fifty mls of LB medium containing ampicillin (100 µg/ml) were inoculated with a fresh glycerol stock of PZ1B. Cells were grown at 30° C. in an incubator shaker to an $OD_{600}$ of 0.7 and stored overnight at 4° C. The following day the cells were pelleted and resuspended in fresh LB medium (no ampicillin). The cells were used to inoculate a 1 liter batch of LB medium and grown at 30° C. in an incubator shaker to an $OD_{600}$ of 1.5. IPTG (SIGMA CHEMICAL, St. Louis, Mo.) was added to a final concentration of 0.1 mM and growth was continued for about 2 to 2.5 hours at which time cells were harvested by centrifugation.

The cell pellet was resuspended in ice cold 1.0M Tris pH 9.0. 2 mM EDTA. The resuspended material is kept on ice for another 20–60 minutes and then centrifuged to separate the periplasmic fraction (supernatant) from the intracellular fraction (pellet).

D. Affinity purification of bFGF-SAP fusion protein

Thirty ml of the dialyzed solution containing the bFGF-SAP fusion protein from Example 2.C. was applied to HiTrap heparin-Sepharose column (Pharmacia, Uppsala, Sweden) equilibrated with 0.15M NaCl in 10 mM TRIS, pH 7.4 (buffer A). The column was washed: first with equilibration buffer; second with 0.6M NaCl in buffer A; third with 1.0M NaCl in buffer A; and finally eluted with 2M NaCl in buffer A into 1.0 ml fractions. Samples were assayed by the ELISA method.

The results indicate that the bFGF-SAP fusion protein elutes from the heparin-Sepharose column at the same concentration (2M NaCl) as native and recombinantly-produced bFGF. This indicates that the heparin affinity is retained in the bFGF-SAP fusion protein.

E. Characterization of the bFGF-SAP fusion protein

1. Western Blot of Affinity-Purified bFGF-SAP Fusion Protein

SDS gel electrophoresis was performed on a Phastsystem utilizing 20% gels (Pharmacia). Western blotting was accomplished by transfer of the electrophoresed protein to nitrocellulose using the PhastTransfer system (Pharmacia), as described by the manufacturer. The antisera to SAP and bFGF were used at a dilution of 1:1000 dilution. Horseradish peroxidase labeled anti-IgG was used as the second antibody (Davis et al. (1986) *Basic Methods in Molecular Biology*, New York, Elsevier Science Publishing Co., pp 1–338).

The anti-SAP and anti-FGF antisera bound to a protein with an approximate molecular weight of 48,000 kd, which corresponds to the sum of the independent molecular weights of SAP (30,000) and bFGF (18,000).

2. Assays to Assess the Cytoxicity of the FGF-SAP Fusion Protein a. Effect of bFGF-SAP Fusion Protein on Cell-Free Protein Synthesis The RIP activity of bFGF-SAP fusion protein compared to the FGF-SAP chemical conjugate was assayed as described in Example 1.G. The results indicated that the $IC_{50}$ of the bFGF-SAP fusion protein is about 0.2 nM and the $IC_{50}$ of chemically conjugated FGF-SAP is about 0.125 nm.

b. Cytotoxicity of bFGF-SAP Fusion Protein

Cytotoxicity experiments were performed with the Promega (Madison, Wis.) CellTiter 96 Cell Proliferation/Cytotoxicity Assay. About 1,500 SK-Mel-28 cells (available from ATCC), a human melanoma cell line, were plated per well in a 96 well plate in 90 µl HDMEM plus 10% FCS and incubated overnight at 37° C., 5% CO2. The following morning 10 µl of media alone or 10 µl of media containing various concentrations of the rbFGF-SAP fusion protein, basic FGF or saporin were added to the wells. The plate was incubated for 72 hours at 37° C. Following the incubation period, the number of living cells was determined by measuring the incorporation and conversion of the commonly available dye MTT supplied as a part of the Promega kit. Fifteen μl of the MTT solution was added to each well, and incubation was continued for 4 hours. Next, 100 μl of the standard solubilization solution supplied as a part of the Promega kit was added to each well. The plate was allowed to stand overnight at room temperature and the absorbance at 560 nm was read on an ELISA plate reader (Titertek Multiskan PLUS, ICN, Flow, Costa Mesa, Calif.).

The results indicated that the chemical FGF-SAP conjugate has an $ID_{50}$ of 0.3 nM, the bFGF-SAP fusion protein has a similar $ID_{50}$ of 0.6 nM, and unconjugated SAP, which is unable to bind to the cell surface, has an $ID_{50}$ of 200 nM. Therefore, when internalized, the bFGF-SAP fusion protein appears to have approximately the same cytotoxic actitivy as the chemically conjugated FGF-SAP.

Since modifications will be apparent to those of skill in this art, it is intended that this invention be limited only by the scope of the appended claims.

We claim:

1. An isolated recombinant DNA fragment, comprising a sequence of nucleotides encoding a saporin-containing protein, wherein:

the saporin-containing protein comprises an N-terminal extension linked to the amino terminus of a saporin protein; and the N-terminal extension and saporin are selected so that the saporin-containing protein is cytotoxic upon internalization by a eukaryotic cell.

2. The DNA fragment of claim 1, further comprising a promoter region and a transcription terminator region, wherein:

the promoter region includes an inducible promoter;

the promoter region and the transcription terminator are independently selected from the same or different genes and are are operatively linked to the DNA encoding the saporin-containing protein.

3. The DNA fragment of claim 1, wherein the N-terminal extension of the saporin-containing protein encodes 2 to 15 amino acids in length.

4. The DNA fragment of claim 3, wherein the sequence of the 2 to 15 amino acids is the same as the sequence of 2 to 15 amino acids of the native secretion signal sequence of the saporin protein.

5. The DNA fragment of claim 1, wherein the N-terminal extension includes a ligand that specifically interacts with a cell surface protein.

6. The DNA fragment of claim 5, wherein the ligand is basic FGF.

7. The DNA fragment of claim 2, wherein the promoter region contains the lac promoter operator (lacO).

8. The DNA fragment of claim 2, wherein the promoter is Ipp.

9. The DNA fragment of claim 1, wherein the amino acid sequence of the saporin-containing protein is set forth in SEQ ID NO. 3, SEQ ID NO. 4, SEQ ID NO. 5, SEQ ID NO. 6 or SEQ ID NO. 7.

10. The DNA fragment of claim 1, wherein the amino acid sequence of the saporin-containing protein is set forth in SEQ ID NO. 12 or SEQ ID NO. 13.

11. The DNA fragment of claim 1, further comprising DNA encoding a secretion signal sequence operatively linked to the DNA encoding the saporin-containing protein.

12. The DNA fragment of claim 11, wherein the secretion signal is ompA or ompT.

13. The DNA fragment of claim 12, wherein the promoter is the T7 promoter or the lacUV5 promoter.

14. A plasmid, comprising the DNA fragment of any of claims 1–13.

15. The plasmid of claim 14, which is selected from the group consisting of pOMPAG4, pOMPAG1, pOMPAG2, pOMPAG7, and pOMPAG9.

16. The plasmid of claim 14 that is PZ1A, PZ1B, PZ1C, or PZID.

17. An *E. coli* cell transformed with the plasmid of claim 14.

18. A culture of viable *E. coli* cells, comprising cells of claim 17.

19. A process for the production of a biologically active saporin-containing protein in *E. coli*, comprising culturing the cells of claim 17 under conditions whereby the saporin-containing protein is expressed, and isolating the saporin-containing protein.

20. The process of claim 19, wherein said N-terminal extension contains a ligand.

21. The process of claim 20, wherein said ligand is a growth factor, hormone, or a cell binding domain of an antibody.

22. The process of claim 20, wherein said ligand is basic fibroblast growth factor (bFGF).

23. An isolated recombinant DNA fragment, comprising a sequence of nucleotides encoding a saporin-containing protein, wherein:

the saporin-containing protein comprises an N-terminal extension linked to the amino terminus of a saporin protein;

the N-terminal extension encodes a site susceptible to cleavage by eukaryotic intracellular proteases; and the saporin-containing protein is cytotoxic upon internalization by a eukaryotic cell.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: misc_recomb
      (B) LOCATION: 6..11
      (D) OTHER INFORMATION: /standard_name= "EcoRI Restriction
         Site"

(ix) FEATURE:
      (A) NAME/KEY: sig_peptide
      (B) LOCATION: 12..30
      (D) OTHER INFORMATION: /function= "N-terminal extension"
         /product= "Native sapor (xi) SEQUENCE DESCRIPTION: SEQ ID NO:1:

CTGCAGAATT CGCATGGATC CTGCTTCAAT                                                                30

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (genomic)

(iv) ANTI-SENSE: YES (ix) FEATURE:
      (A) NAME/KEY: misc_recomb
      (B) LOCATION: 6..11
      (D) OTHER INFORMATION: /standard_name= "EcoRI Restriction
         Site"

(ix) FEATURE:
      (A) NAME/KEY: terminator
      (B) LOCATION: 23..25
      (D) OTHER INFORMATION: /note= "Anti-sense stop codon"

(ix) FEATURE:
      (A) NAME/KEY: mat_peptide (B) LOCATION: 26..30
(D) OTHER INFORMATION: /note= "Anti-sense to carboxyl
    terminus of mature peptide"

(xi) SEQUENCE DESCRIPTION: SEQ ID NO:2:

CTGCAGAATT CGCCTCGTTT GACTACTTTG                                    30

(2) INFORMATION FOR SEQ ID NO:3:

(i) SEQUENCE CHARACTERISTICS:
        (A) LENGTH: 804 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..804

(ix) FEATURE:
        (A) NAME/KEY: misc_feature
        (B) LOCATION: 1..804
        (D) OTHER INFORMATION: /note= "Nucleotide sequence
            corresponding to the clone M13 mp18-G4 in Example 1.B.2."

(ix) FEATURE:
        (A) NAME/KEY: mat_peptide
        (B) LOCATION: 46..804
        (D) OTHER INFORMATION: /product= ""Saporin""

(xi) SEQUENCE DESCRIPTION: SEQ ID NO:3:

```
GCA TGG ATC CTG CTT CAA TTT TCA GCT TGG ACA ACA ACT GAT GCG GTC       48
Ala Trp Ile Leu Leu Gln Phe Ser Ala Trp Thr Thr Thr Asp Ala Val
-15             -10                 -5                   1

ACA TCA ATC ACA TTA GAT CTA GTA AAT CCG ACC GCG GGT CAA TAC TCA       96
Thr Ser Ile Thr Leu Asp Leu Val Asn Pro Thr Ala Gly Gln Tyr Ser
            5                   10                  15

TCT TTT GTG GAT AAA ATC CGA AAC AAT GTA AAG GAT CCA AAC CTG AAA      144
Ser Phe Val Asp Lys Ile Arg Asn Asn Val Lys Asp Pro Asn Leu Lys
        20                  25                  30

TAC GGT GGT ACC GAC ATA GCC GTG ATA GGC CCA CCT TCT AAA GAA AAA      192
Tyr Gly Gly Thr Asp Ile Ala Val Ile Gly Pro Pro Ser Lys Glu Lys
    35                  40                  45

TTC CTT AGA ATT AAT TTC CAA AGT TCC CGA GGA ACG GTC TCA CTT GGC      240
Phe Leu Arg Ile Asn Phe Gln Ser Ser Arg Gly Thr Val Ser Leu Gly
50                  55                  60                  65

CTA AAA CGC GAT AAC TTG TAT GTG GTC GCG TAT CTT GCA ATG GAT AAC      288
Leu Lys Arg Asp Asn Leu Tyr Val Val Ala Tyr Leu Ala Met Asp Asn
            70                  75                  80

ACG AAT GTT AAT CGG GCA TAT TAC TTC AAA TCA GAA ATT ACT TCC GCC      336
Thr Asn Val Asn Arg Ala Tyr Tyr Phe Lys Ser Glu Ile Thr Ser Ala
        85                  90                  95

GAG TTA ACC GCC CTT TTC CCA GAG GCC ACA ACT GCA AAT CAG AAA GCT      384
Glu Leu Thr Ala Leu Phe Pro Glu Ala Thr Thr Ala Asn Gln Lys Ala
    100                 105                 110

TTA GAA TAC ACA GAA GAT TAT CAG TCG ATC GAA AAG AAT GCC CAG ATA      432
Leu Glu Tyr Thr Glu Asp Tyr Gln Ser Ile Glu Lys Asn Ala Gln Ile
115                 120                 125

ACA CAG GGA GAT AAA AGT AGA AAA GAA CTC GGG TTG GGG ATC GAC TTA      480
Thr Gln Gly Asp Lys Ser Arg Lys Glu Leu Gly Leu Gly Ile Asp Leu
130                 135                 140                 145

CTT CTT ACG TTC ATG GAA GCA GTG AAC AAG AAG GCA CGT GTG GTT AAA      528
Leu Leu Thr Phe Met Glu Ala Val Asn Lys Lys Ala Arg Val Val Lys
            150                 155                 160
```

-continued

```
AAC GAA GCT AGG TTT CTG CTT ATC GCT ATT CAA ATG ACA GCT GAG GTA       576
Asn Glu Ala Arg Phe Leu Leu Ile Ala Ile Gln Met Thr Ala Glu Val
            165                 170                 175

GCA CGA TTT AGG TAC ATT CAA AAC TTG GTA ACT AAG AAC TTC CCC AAC       624
Ala Arg Phe Arg Tyr Ile Gln Asn Leu Val Thr Lys Asn Phe Pro Asn
            180                 185                 190

AAG TTC GAC TCG GAT AAC AAG GTG ATT CAA TTT GAA GTC AGC TGG CGT       672
Lys Phe Asp Ser Asp Asn Lys Val Ile Gln Phe Glu Val Ser Trp Arg
            195                 200                 205

AAG ATT TCT ACG GCA ATA TAC GGG GAT GCC AAA AAC GGC GTG TTT AAT       720
Lys Ile Ser Thr Ala Ile Tyr Gly Asp Ala Lys Asn Gly Val Phe Asn
210                 215                 220                 225

AAA GAT TAT GAT TTC GGG TTT GGA AAA GTG AGG CAG GTG AAG GAC TTG       768
Lys Asp Tyr Asp Phe Gly Phe Gly Lys Val Arg Gln Val Lys Asp Leu
                230                 235                 240

CAA ATG GGA CTC CTT ATG TAT TTG GGC AAA CCA AAG                       804
Gln Met Gly Leu Leu Met Tyr Leu Gly Lys Pro Lys
            245                 250
```

(2) INFORMATION FOR SEQ ID NO:4:

(i) SEQUENCE CHARACTERISTICS:
        (A) LENGTH: 804 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..804

(ix) FEATURE:
        (A) NAME/KEY: misc_feature
        (B) LOCATION: 1..804
        (D) OTHER INFORMATION: /note= "Nucleotide sequence
            corresponding to the clone M13 mp18-G1 in Example 1.B.2."

(ix) FEATURE:
        (A) NAME/KEY: mat_peptide
        (B) LOCATION: 46..804
        (D) OTHER INFORMATION: /product= "Saporin"

(xi) SEQUENCE DESCRIPTION: SEQ ID NO:4:

```
GCA TGG ATC CTG CTT CAA TTT TCA GCT TGG ACA ACA ACT GAT GCG GTC        48
Ala Trp Ile Leu Leu Gln Phe Ser Ala Trp Thr Thr Thr Asp Ala Val
-15             -10                 -5                           1

ACA TCA ATC ACA TTA GAT CTA GTA AAT CCG ACC GCG GGT CAA TAC TCA        96
Thr Ser Ile Thr Leu Asp Leu Val Asn Pro Thr Ala Gly Gln Tyr Ser
              5                  10                  15

TCT TTT GTG GAT AAA ATC CGA AAC AAC GTA AAG GAT CCA AAC CTG AAA       144
Ser Phe Val Asp Lys Ile Arg Asn Asn Val Lys Asp Pro Asn Leu Lys
            20                  25                  30

TAC GGT GGT ACC GAC ATA GCC GTG ATA GGC CCA CCT TCT AAA GAA AAA       192
Tyr Gly Gly Thr Asp Ile Ala Val Ile Gly Pro Pro Ser Lys Glu Lys
        35                  40                  45

TTC CTT AGA ATT AAT TTC CAA AGT TCC CGA GGA ACG GTC TCA CTT GGC       240
Phe Leu Arg Ile Asn Phe Gln Ser Ser Arg Gly Thr Val Ser Leu Gly
50                  55                  60                  65

CTA AAA CGC GAT AAC TTG TAT GTG GTC GCG TAT CTT GCA ATG GAT AAC       288
Leu Lys Arg Asp Asn Leu Tyr Val Val Ala Tyr Leu Ala Met Asp Asn
                70                  75                  80

ACG AAT GTT AAT CGG GCA TAT TAC TTC AGA TCA GAA ATT ACT TCC GCC       336
Thr Asn Val Asn Arg Ala Tyr Tyr Phe Arg Ser Glu Ile Thr Ser Ala
            85                  90                  95
```

```
GAG TTA ACC GCC CTT TTC CCA GAG GCC ACA ACT GCA AAT CAG AAA GCT       384
Glu Leu Thr Ala Leu Phe Pro Glu Ala Thr Thr Ala Asn Gln Lys Ala
            100                 105                 110

TTA GAA TAC ACA GAA GAT TAT CAG TCG ATC GAA AAG AAT GCC CAG ATA       432
Leu Glu Tyr Thr Glu Asp Tyr Gln Ser Ile Glu Lys Asn Ala Gln Ile
115                 120                 125

ACA CAG GGA GAT AAA TCA AGA AAA GAA CTC GGG TTG GGG ATC GAC TTA       480
Thr Gln Gly Asp Lys Ser Arg Lys Glu Leu Gly Leu Gly Ile Asp Leu
130                 135                 140                 145

CTT TTG ACG TCC ATG GAA GCA GTG AAC AAG AAG GCA CGT GTG GTT AAA       528
Leu Leu Thr Ser Met Glu Ala Val Asn Lys Lys Ala Arg Val Val Lys
                150                 155                 160

AAC GAA GCT AGG TTT CTG CTT ATC GCT ATT CAA ATG ACA GCT GAG GTA       576
Asn Glu Ala Arg Phe Leu Leu Ile Ala Ile Gln Met Thr Ala Glu Val
            165                 170                 175

GCA CGA TTT CGG TAC ATT CAA AAC TTG GTA ACT AAG AAC TTC CCC AAC       624
Ala Arg Phe Arg Tyr Ile Gln Asn Leu Val Thr Lys Asn Phe Pro Asn
        180                 185                 190

AAG TTC GAC TCG GAT AAC AAG GTG ATT CAA TTT GAA GTC AGC TGG CGT       672
Lys Phe Asp Ser Asp Asn Lys Val Ile Gln Phe Glu Val Ser Trp Arg
    195                 200                 205

AAG ATT TCT ACG GCA ATA TAC GGA GAT GCC AAA AAC GGC GTG TTT AAT       720
Lys Ile Ser Thr Ala Ile Tyr Gly Asp Ala Lys Asn Gly Val Phe Asn
210                 215                 220                 225

AAA GAT TAT GAT TTC GGG TTT GGA AAA GTG AGG CAG GTG AAG GAC TTG       768
Lys Asp Tyr Asp Phe Gly Phe Gly Lys Val Arg Gln Val Lys Asp Leu
                230                 235                 240

CAA ATG GGA CTC CTT ATG TAT TTG GGC AAA CCA AAG                       804
Gln Met Gly Leu Leu Met Tyr Leu Gly Lys Pro Lys
            245                 250
```

(2) INFORMATION FOR SEQ ID NO:5:

(i) SEQUENCE CHARACTERISTICS:
        (A) LENGTH: 804 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..804

(ix) FEATURE:
        (A) NAME/KEY: misc_feature
        (B) LOCATION: 1..804
        (D) OTHER INFORMATION: /note= "Nucleotide sequence
            corresponding to the clone M13 mp18-G2 in Example 1.B.2."

(ix) FEATURE:
        (A) NAME/KEY: mat_peptide
        (B) LOCATION: 46..804
        (D) OTHER INFORMATION: /product= "Saporin"

(xi) SEQUENCE DESCRIPTION: SEQ ID NO:5:

```
GCA TGG ATC CTG CTT CAA TTT TCA GCT TGG ACA ACA ACT GAT GCG GTC        48
Ala Trp Ile Leu Leu Gln Phe Ser Ala Trp Thr Thr Thr Asp Ala Val
-15                 -10                 -5                   1

ACA TCA ATC ACA TTA GAT CTA GTA AAT CCG ACT GCG GGT CAA TAC TCA        96
Thr Ser Ile Thr Leu Asp Leu Val Asn Pro Thr Ala Gly Gln Tyr Ser
                5                   10                  15

TCT TTT GTG GAT AAA ATC CGA AAC AAC GTA AAG GAT CCA AAC CTG AAA       144
Ser Phe Val Asp Lys Ile Arg Asn Asn Val Lys Asp Pro Asn Leu Lys
            20                  25                  30
```

```
TAC GGT GGT ACC GAC ATA GCC GTG ATA GGC CCA CCT TCT AAA GAT AAA        192
Tyr Gly Gly Thr Asp Ile Ala Val Ile Gly Pro Pro Ser Lys Asp Lys
 35                  40                  45

TTC CTT AGA ATT AAT TTC CAA AGT TCC CGA GGA ACG GTC TCA CTT GGC        240
Phe Leu Arg Ile Asn Phe Gln Ser Ser Arg Gly Thr Val Ser Leu Gly
 50                  55                  60                  65

CTA AAA CGC GAT AAC TTG TAT GTG GTC GCG TAT CTT GCA ATG GAT AAC        288
Leu Lys Arg Asp Asn Leu Tyr Val Val Ala Tyr Leu Ala Met Asp Asn
                 70                  75                  80

ACG AAT GTT AAT CGG GCA TAT TAC TTC AAA TCA GAA ATT ACT TCC GCC        336
Thr Asn Val Asn Arg Ala Tyr Tyr Phe Lys Ser Glu Ile Thr Ser Ala
                 85                  90                  95

GAG TTA ACC GCC CTT TTC CCA GAG GCC ACA ACT GCA AAT CAG AAA GCT        384
Glu Leu Thr Ala Leu Phe Pro Glu Ala Thr Thr Ala Asn Gln Lys Ala
            100                 105                 110

TTA GAA TAC ACA GAA GAT TAT CAG TCG ATC GAA AAG AAT GCC CAG ATA        432
Leu Glu Tyr Thr Glu Asp Tyr Gln Ser Ile Glu Lys Asn Ala Gln Ile
            115                 120                 125

ACA CAG GGA GAT AAA AGT AGA AAA GAA CTC GGG TTG GGG ATC GAC TTA        480
Thr Gln Gly Asp Lys Ser Arg Lys Glu Leu Gly Leu Gly Ile Asp Leu
130                 135                 140                 145

CTT TTG ACG TTC ATG GAA GCA GTG AAC AAG AAG GCA CGT GTG GTT AAA        528
Leu Leu Thr Phe Met Glu Ala Val Asn Lys Lys Ala Arg Val Val Lys
                150                 155                 160

AAC GAA GCT AGG TTT CTG CTT ATC GCT ATT CAA ATG ACA GCT GAG GTA        576
Asn Glu Ala Arg Phe Leu Leu Ile Ala Ile Gln Met Thr Ala Glu Val
                165                 170                 175

GCA CGA TTT AGG TAC ATT CAA AAC TTG GTA ACT AAG AAC TTC CCC AAC        624
Ala Arg Phe Arg Tyr Ile Gln Asn Leu Val Thr Lys Asn Phe Pro Asn
            180                 185                 190

AAG TTC GAC TCG GAT AAC AAG GTG ATT CAA TTT GAA GTC AGC TGG CGT        672
Lys Phe Asp Ser Asp Asn Lys Val Ile Gln Phe Glu Val Ser Trp Arg
195                 200                 205

AAG ATT TCT ACG GCA ATA TAC GGG GAT GCC AAA AAC GGC GTG TTT AAT        720
Lys Ile Ser Thr Ala Ile Tyr Gly Asp Ala Lys Asn Gly Val Phe Asn
210                 215                 220                 225

AAA GAT TAT GAT TTC GGG TTT GGA AAA GTG AGG CAG GTG AAG GAC TTG        768
Lys Asp Tyr Asp Phe Gly Phe Gly Lys Val Arg Gln Val Lys Asp Leu
                230                 235                 240

CAA ATG GGA CTC CTT ATG TAT TTG GGC AAA CCA AAG                        804
Gln Met Gly Leu Leu Met Tyr Leu Gly Lys Pro Lys
            245                 250
```

(2) INFORMATION FOR SEQ ID NO:6:

(i) SEQUENCE CHARACTERISTICS:
        (A) LENGTH: 804 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..804

(ix) FEATURE:
        (A) NAME/KEY: misc_feature
        (B) LOCATION: 1..804
        (D) OTHER INFORMATION: /note= "Nucleotide sequence
            corresponding to the clone M13 mp18-G7 in Example 1.B.2."

(ix) FEATURE:
        (A) NAME/KEY: mat_peptide
        (B) LOCATION: 46..804

(D) OTHER INFORMATION: /product= "Saporin"

(xi) SEQUENCE DESCRIPTION: SEQ ID NO:6:

| | | | | | | | | | | | | | | | | |
|---|---|---|---|---|---|---|---|---|---|---|---|---|---|---|---|---|
| GCA | TGG | ATC | CTG | CTT | CAA | TTT | TCA | GCT | TGG | ACA | ACA | ACT | GAT | GCG | GTC | 48 |
| Ala | Trp | Ile | Leu | Leu | Gln | Phe | Ser | Ala | Trp | Thr | Thr | Thr | Asp | Ala | Val | |
| -15 | | | | -10 | | | | -5 | | | | | | | 1 | |
| ACA | TCA | ATC | ACA | TTA | GAT | CTA | GTA | AAT | CCG | ACC | GCG | GGT | CAA | TAC | TCA | 96 |
| Thr | Ser | Ile | Thr | Leu | Asp | Leu | Val | Asn | Pro | Thr | Ala | Gly | Gln | Tyr | Ser | |
| | | | 5 | | | | | 10 | | | | | 15 | | | |
| TCT | TTT | GTG | GAT | AAA | ATC | CGA | AAC | AAC | GTA | AAG | GAT | CCA | AAC | CTG | AAA | 144 |
| Ser | Phe | Val | Asp | Lys | Ile | Arg | Asn | Asn | Val | Lys | Asp | Pro | Asn | Leu | Lys | |
| | | | 20 | | | | 25 | | | | | 30 | | | | |
| TAC | GGT | GGT | ACC | GAC | ATA | GCC | GTG | ATA | GGC | CCA | CCT | TCT | AAA | GAA | AAA | 192 |
| Tyr | Gly | Gly | Thr | Asp | Ile | Ala | Val | Ile | Gly | Pro | Pro | Ser | Lys | Glu | Lys | |
| | 35 | | | | 40 | | | | | 45 | | | | | | |
| TTC | CTT | AGA | ATT | AAT | TTC | CAA | AGT | TCC | CGA | GGA | ACG | GTC | TCA | CTT | GGC | 240 |
| Phe | Leu | Arg | Ile | Asn | Phe | Gln | Ser | Ser | Arg | Gly | Thr | Val | Ser | Leu | Gly | |
| 50 | | | | | 55 | | | | | 60 | | | | | 65 | |
| CTA | AAA | CGC | GAT | AAC | TTG | TAT | GTG | GTC | GCG | TAT | CTT | GCA | ATG | GAT | AAC | 288 |
| Leu | Lys | Arg | Asp | Asn | Leu | Tyr | Val | Val | Ala | Tyr | Leu | Ala | Met | Asp | Asn | |
| | | | | 70 | | | | | 75 | | | | | 80 | | |
| ACG | AAT | GTT | AAT | CGG | GCA | TAT | TAC | TTC | AGA | TCA | GAA | ATT | ACT | TCC | GCC | 336 |
| Thr | Asn | Val | Asn | Arg | Ala | Tyr | Tyr | Phe | Arg | Ser | Glu | Ile | Thr | Ser | Ala | |
| | | | | 85 | | | | | 90 | | | | | 95 | | |
| GAG | TTA | ACC | GCC | CTT | TTC | CCA | GAG | GCC | ACA | ACT | GCA | AAT | CAG | AAA | GCT | 384 |
| Glu | Leu | Thr | Ala | Leu | Phe | Pro | Glu | Ala | Thr | Thr | Ala | Asn | Gln | Lys | Ala | |
| | | | 100 | | | | | 105 | | | | | 110 | | | |
| TTA | GAA | TAC | ACA | GAA | GAT | TAT | CAG | TCG | ATC | GAA | AAG | AAT | GCC | CAG | ATA | 432 |
| Leu | Glu | Tyr | Thr | Glu | Asp | Tyr | Gln | Ser | Ile | Glu | Lys | Asn | Ala | Gln | Ile | |
| | 115 | | | | | 120 | | | | | 125 | | | | | |
| ACA | CAG | GGA | GAT | AAA | TCA | AGA | AAA | GAA | CTC | GGG | TTG | GGG | ATC | GAC | TTA | 480 |
| Thr | Gln | Gly | Asp | Lys | Ser | Arg | Lys | Glu | Leu | Gly | Leu | Gly | Ile | Asp | Leu | |
| 130 | | | | | 135 | | | | | 140 | | | | | 145 | |
| CTT | TTG | ACG | TCC | ATG | GAA | GCA | GTG | AAC | AAG | AAG | GCA | CGT | GTG | GTT | AAA | 528 |
| Leu | Leu | Thr | Ser | Met | Glu | Ala | Val | Asn | Lys | Lys | Ala | Arg | Val | Val | Lys | |
| | | | | 150 | | | | | 155 | | | | | 160 | | |
| AAC | GAA | GCT | AGA | TTC | CTT | CTT | ATC | GCT | ATT | CAG | ATG | ACG | GCT | GAG | GCA | 576 |
| Asn | Glu | Ala | Arg | Phe | Leu | Leu | Ile | Ala | Ile | Gln | Met | Thr | Ala | Glu | Ala | |
| | | | 165 | | | | | 170 | | | | | 175 | | | |
| GCA | CGA | TTT | AGG | TAC | ATA | CAA | AAC | TTG | GTA | ATC | AAG | AAC | TTT | CCC | AAC | 624 |
| Ala | Arg | Phe | Arg | Tyr | Ile | Gln | Asn | Leu | Val | Ile | Lys | Asn | Phe | Pro | Asn | |
| | | 180 | | | | | 185 | | | | | 190 | | | | |
| AAG | TTC | AAC | TCG | GAA | AAC | AAA | GTG | ATT | CAG | TTT | GAG | GTT | AAC | TGG | AAA | 672 |
| Lys | Phe | Asn | Ser | Glu | Asn | Lys | Val | Ile | Gln | Phe | Glu | Val | Asn | Trp | Lys | |
| | 195 | | | | | 200 | | | | | 205 | | | | | |
| AAA | ATT | TCT | ACG | GCA | ATA | TAC | GGG | GAT | GCC | AAA | AAC | GGC | GTG | TTT | AAT | 720 |
| Lys | Ile | Ser | Thr | Ala | Ile | Tyr | Gly | Asp | Ala | Lys | Asn | Gly | Val | Phe | Asn | |
| 210 | | | | | 215 | | | | | 220 | | | | | 225 | |
| AAA | GAT | TAT | GAT | TTC | GGG | TTT | GGA | AAA | GTG | AGG | CAG | GTG | AAG | GAC | TTG | 768 |
| Lys | Asp | Tyr | Asp | Phe | Gly | Phe | Gly | Lys | Val | Arg | Gln | Val | Lys | Asp | Leu | |
| | | | 230 | | | | | 235 | | | | | 240 | | | |
| CAA | ATG | GGA | CTC | CTT | ATG | TAT | TTG | GGC | AAA | CCA | AAG | | | | | 804 |
| Gln | Met | Gly | Leu | Leu | Met | Tyr | Leu | Gly | Lys | Pro | Lys | | | | | |
| | | | 245 | | | | | 250 | | | | | | | | |

(2) INFORMATION FOR SEQ ID NO:7:

(i) SEQUENCE CHARACTERISTICS:
        (A) LENGTH: 804 base pairs
        (B) TYPE: nucleic acid
        (C) STRANDEDNESS: double
        (D) TOPOLOGY: unknown (ii) MOLECULE TYPE: cDNA (ix) FEATURE:
    (A) NAME/KEY: CDS
    (B) LOCATION: 1..804

(ix) FEATURE:
    (A) NAME/KEY: misc_feature
    (B) LOCATION: 1..804
    (D) OTHER INFORMATION: /note= "Nucleotide sequence
        corresponding to the clone M13 mp18-G9 in Example 1.B.2."

(ix) FEATURE:
    (A) NAME/KEY: mat_peptide
    (B) LOCATION: 46..804
    (D) OTHER INFORMATION: /product= "Saporin"

(xi) SEQUENCE DESCRIPTION: SEQ ID NO:7:

```
GCA TGG ATC CTG CTT CAA TTT TCA GCT TGG ACA ACA ACT GAT GCG GTC         48
Ala Trp Ile Leu Leu Gln Phe Ser Ala Trp Thr Thr Thr Asp Ala Val
-15             -10                 -5                    1

ACA TCA ATC ACA TTA GAT CTA GTA AAT CCG ACC GCG GGT CAA TAC TCA         96
Thr Ser Ile Thr Leu Asp Leu Val Asn Pro Thr Ala Gly Gln Tyr Ser
            5                   10                  15

TCT TTT GTG GAT AAA ATC CGA AAC AAC GTA AAG GAT CCA AAC CTG AAA        144
Ser Phe Val Asp Lys Ile Arg Asn Asn Val Lys Asp Pro Asn Leu Lys
        20                  25                  30

TAC GGT GGT ACC GAC ATA GCC GTG ATA GGC CCA CCT TCT AAA GAA AAA        192
Tyr Gly Gly Thr Asp Ile Ala Val Ile Gly Pro Pro Ser Lys Glu Lys
    35                  40                  45

TTC CTT AGA ATT AAT TTC CAA AGT TCC CGA GGA ACG TCA CTT GGC            240
Phe Leu Arg Ile Asn Phe Gln Ser Ser Arg Gly Thr Val Ser Leu Gly
50                  55                  60                  65

CTA AAA CGC GAT AAC TTG TAT GTG GTC GCG TAT CTT GCA ATG GAT AAC        288
Leu Lys Arg Asp Asn Leu Tyr Val Val Ala Tyr Leu Ala Met Asp Asn
            70                  75                  80

ACG AAT GTT AAT CGG GCA TAT TAC TTC AGA TCA GAA ATT ACT TCC GCC        336
Thr Asn Val Asn Arg Ala Tyr Tyr Phe Arg Ser Glu Ile Thr Ser Ala
        85                  90                  95

GAG TTA ACC GCC CTT TTC CCA GAG GCC ACA ACT GCA AAT CAG AAA GCT        384
Glu Leu Thr Ala Leu Phe Pro Glu Ala Thr Thr Ala Asn Gln Lys Ala
    100                 105                 110

TTA GAA TAC ACA GAA GAT TAT CAG TCG ATT GAA AAG AAT GCC CAG ATA        432
Leu Glu Tyr Thr Glu Asp Tyr Gln Ser Ile Glu Lys Asn Ala Gln Ile
115                 120                 125

ACA CAA GGA GAT CAA AGT AGA AAA GAA CTC GGG TTG GGG ATT GAC TTA        480
Thr Gln Gly Asp Gln Ser Arg Lys Glu Leu Gly Leu Gly Ile Asp Leu
130             135                 140                 145

CTT TCA ACG TCC ATG GAA GCA GTG AAC AAG AAG GCA CGT GTG GTT AAA        528
Leu Ser Thr Ser Met Glu Ala Val Asn Lys Lys Ala Arg Val Val Lys
            150                 155                 160

GAC GAA GCT AGA TTC CTT CTT ATC GCT ATT CAG ATG ACG GCT GAG GCA        576
Asp Glu Ala Arg Phe Leu Leu Ile Ala Ile Gln Met Thr Ala Glu Ala
        165                 170                 175

GCG CGA TTT AGG TAC ATA CAA AAC TTG GTA ATC AAG AAC TTT CCC AAC        624
Ala Arg Phe Arg Tyr Ile Gln Asn Leu Val Ile Lys Asn Phe Pro Asn
    180                 185                 190

AAG TTC AAC TCG GAA AAC AAA GTG ATT CAG TTT GAG GTT AAC TGG AAA        672
Lys Phe Asn Ser Glu Asn Lys Val Ile Gln Phe Glu Val Asn Trp Lys
195                 200                 205

AAA ATT TCT ACG GCA ATA TAC GGG GAT GCC AAA AAC GGC GTG TTT AAT        720
Lys Ile Ser Thr Ala Ile Tyr Gly Asp Ala Lys Asn Gly Val Phe Asn
210             215                 220                 225
```

```
AAA GAT TAT GAT TTC GGG TTT GGA AAA GTG AGG CAG GTG AAG GAC TTG      768
Lys Asp Tyr Asp Phe Gly Phe Gly Lys Val Arg Gln Val Lys Asp Leu
            230                 235                 240

CAA ATG GGA CTC CTT ATG TAT TTG GGC AAA CCA AAG                      804
Gln Met Gly Leu Leu Met Tyr Leu Gly Lys Pro Lys
        245                 250
```

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_recomb
        (B) LOCATION: 10..15
        (D) OTHER INFORMATION: /standard_name= "Nco I restriction
            enzyme recognition site (ix) FEATURE:
        (A) NAME/KEY: mat_peptide
        (B) LOCATION: 15..22
        (D) OTHER INFORMATION: /product= "N-terminus of Saporin
            protein"

(xi) SEQUENCE DESCRIPTION: SEQ ID NO:8:

```
CAACAACTGC CATGGTCACA TC                                              22
```

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_recomb
        (B) LOCATION: 11..16
        (D) OTHER INFORMATION: /standard_name= "Nco I restriction
            enzyme recognition site (ix) FEATURE:
        (A) NAME/KEY: mat_peptide
        (B) LOCATION: 1..10
        (D) OTHER INFORMATION: /product= "Carboxy terminus of
            mature FGF protein"

(xi) SEQUENCE DESCRIPTION: SEQ ID NO:9:

```
GCTAAGAGCG CCATGGAGA                                                  19
```

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..12
        (D) OTHER INFORMATION: /product= "Carboxy terminus of
            wild type FGF"

(ix) FEATURE:

(A) NAME/KEY: misc_recomb
            (B) LOCATION: 13..18
            (D) OTHER INFORMATION: /standard_name= "Nco I restriction
                enzyme recognition site (xi) SEQUENCE DESCRIPTION: SEQ ID NO:10:

```
GCT AAG AGC TGACCATGGA GA                                              21
Ala Lys Ser
 1
```

(2) INFORMATION FOR SEQ ID NO:11:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..96
        (D) OTHER INFORMATION: /product= "pFGFNcoI"
            /note= "Equals the plasmid pFC80 with native FGF
            stop codon removed."

(ix) FEATURE:
        (A) NAME/KEY: misc_recomb
        (B) LOCATION: 29..34
        (D) OTHER INFORMATION: /standard_name= "Nco I restriction
            enzyme recognition site (xi) SEQUENCE DESCRIPTION: SEQ ID NO:11:

```
CTT TTT CTT CCA ATG TCT GCT AAG AGC GCC ATG GAG ATC CGG CTG AAT        48
Leu Phe Leu Pro Met Ser Ala Lys Ser Ala Met Glu Ile Arg Leu Asn
 1               5                  10                  15

GGT GCA GTT CTG TAC CGG TTT TCC TGT GCC GTC TTT CAG GAC TCC TGAAAT    102
Gly Ala Val Leu Tyr Arg Phe Ser Cys Ala Val Phe Gln Asp Ser
            20                  25                  30

CTT
```

(2) INFORMATION FOR SEQ ID NO:12:

(i) SEQUENCE CHARACTERISTICS:
        (A) LENGTH: 1230 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..1230

(ix) FEATURE:
        (A) NAME/KEY: mat_peptide
        (B) LOCATION: 1..465
        (D) OTHER INFORMATION: /product= "bFGF"

(ix) FEATURE:
        (A) NAME/KEY: mat_peptide
        (B) LOCATION: 472..1230
        (D) OTHER INFORMATION: /product= "Saporin"

(xi) SEQUENCE DESCRIPTION: SEQ ID NO:12:

```
ATG GCA GCA GGA TCA ATA ACA ACA TTA CCC GCC TTG CCC GAG GAT GGC        48
Met Ala Ala Gly Ser Ile Thr Thr Leu Pro Ala Leu Pro Glu Asp Gly
 1               5                  10                  15

GGC AGC GGC GCC TTC CCG CCC GGC CAC TTC AAG GAC CCC AAG CGG CTG        96
Gly Ser Gly Ala Phe Pro Pro Gly His Phe Lys Asp Pro Lys Arg Leu
```

|  |  |  |  |  |  |  |  |  |  |  |  |  |  |  |  |
|---|---|---|---|---|---|---|---|---|---|---|---|---|---|---|---|
|  |  |  | 20 |  |  |  |  | 25 |  |  |  |  | 30 |  |  |

```
TAC TGC AAA AAC GGG GGC TTC TTC CTG CGC ATC CAC CCC GAC GGC CGA        144
Tyr Cys Lys Asn Gly Gly Phe Phe Leu Arg Ile His Pro Asp Gly Arg
         35                  40                  45

GTT GAC GGG GTC CGG GAG AAG AGC GAC CCT CAC ATC AAG CTT CAA CTT        192
Val Asp Gly Val Arg Glu Lys Ser Asp Pro His Ile Lys Leu Gln Leu
         50                  55                  60

CAA GCA GAA GAG AGA GGA GTT GTG TCT ATC AAA GGA GTG TGT GCT AAC        240
Gln Ala Glu Glu Arg Gly Val Val Ser Ile Lys Gly Val Cys Ala Asn
 65                  70                  75                  80

CGT TAC CTG GCT ATG AAG GAA GAT GGA AGA TTA CTG GCT TCT AAA TGT        288
Arg Tyr Leu Ala Met Lys Glu Asp Gly Arg Leu Leu Ala Ser Lys Cys
                     85                  90                  95

GTT ACG GAT GAG TGT TTC TTT TTT GAA CGA TTG GAA TCT AAT AAC TAC        336
Val Thr Asp Glu Cys Phe Phe Phe Glu Arg Leu Glu Ser Asn Asn Tyr
                 100                 105                 110

AAT ACT TAC CGG TCA AGG AAA TAC ACC AGT TGG TAT GTG GCA TTG AAA        384
Asn Thr Tyr Arg Ser Arg Lys Tyr Thr Ser Trp Tyr Val Ala Leu Lys
             115                 120                 125

CGA ACT GGG CAG TAT AAA CTT GGA TCC AAA ACA GGA CCT GGG CAG AAA        432
Arg Thr Gly Gln Tyr Lys Leu Gly Ser Lys Thr Gly Pro Gly Gln Lys
         130                 135                 140

GCT ATA CTT TTT CTT CCA ATG TCT GCT AAG AGC GCC ATG GTC ACA TCA        480
Ala Ile Leu Phe Leu Pro Met Ser Ala Lys Ser Ala Met Val Thr Ser
145                 150                 155                 160

ATC ACA TTA GAT CTA GTA AAT CCG ACC GCG GGT CAA TAC TCA TCT TTT        528
Ile Thr Leu Asp Leu Val Asn Pro Thr Ala Gly Gln Tyr Ser Ser Phe
                 165                 170                 175

GTG GAT AAA ATC CGA AAC AAC GTA AAG GAT CCA AAC CTG AAA TAC GGT        576
Val Asp Lys Ile Arg Asn Asn Val Lys Asp Pro Asn Leu Lys Tyr Gly
             180                 185                 190

GGT ACC GAC ATA GCC GTG ATA GGC CCA CCT TCT AAA GAA AAA TTC CTT        624
Gly Thr Asp Ile Ala Val Ile Gly Pro Pro Ser Lys Glu Lys Phe Leu
         195                 200                 205

AGA ATT AAT TTC CAA AGT TCC CGA GGA ACG GTC TCA CTT GGC CTA AAA        672
Arg Ile Asn Phe Gln Ser Ser Arg Gly Thr Val Ser Leu Gly Leu Lys
210                 215                 220

CGC GAT AAC TTG TAT GTG GTC GCG TAT CTT GCA ATG GAT AAC ACG AAT        720
Arg Asp Asn Leu Tyr Val Val Ala Tyr Leu Ala Met Asp Asn Thr Asn
225                 230                 235                 240

GTT AAT CGG GCA TAT TAC TTC AAA TCA GAA ATT ACT TCC GCC GAG TTA        768
Val Asn Arg Ala Tyr Tyr Phe Lys Ser Glu Ile Thr Ser Ala Glu Leu
                 245                 250                 255

ACC GCC CTT TTC CCA GAG GCC ACA ACT GCA AAT CAG AAA GCT TTA GAA        816
Thr Ala Leu Phe Pro Glu Ala Thr Thr Ala Asn Gln Lys Ala Leu Glu
             260                 265                 270

TAC ACA GAA GAT TAT CAG TCG ATC GAA AAG AAT GCC CAG ATA ACA CAG        864
Tyr Thr Glu Asp Tyr Gln Ser Ile Glu Lys Asn Ala Gln Ile Thr Gln
         275                 280                 285

GGA GAT AAA AGT AGA AAA GAA CTC GGG TTG GGG ATC GAC TTA CTT TTG        912
Gly Asp Lys Ser Arg Lys Glu Leu Gly Leu Gly Ile Asp Leu Leu Leu
290                 295                 300

ACG TTC ATG GAA GCA GTG AAC AAG AAG GCA CGT GTG GTT AAA AAC GAA        960
Thr Phe Met Glu Ala Val Asn Lys Lys Ala Arg Val Val Lys Asn Glu
305                 310                 315                 320

GCT AGG TTT CTG CTT ATC GCT ATT CAA ATG ACA GCT GAG GTA GCA CGA       1008
Ala Arg Phe Leu Leu Ile Ala Ile Gln Met Thr Ala Glu Val Ala Arg
                 325                 330                 335

TTT AGG TAC ATT CAA AAC TTG GTA ACT AAG AAC TTC CCC AAC AAG TTC       1056
Phe Arg Tyr Ile Gln Asn Leu Val Thr Lys Asn Phe Pro Asn Lys Phe
```

```
                               340                345                350
GAC TCG GAT AAC AAG GTG ATT CAA TTT GAA GTC AGC TGG CGT AAG ATT       1104
Asp Ser Asp Asn Lys Val Ile Gln Phe Glu Val Ser Trp Arg Lys Ile
            355                360                365

TCT ACG GCA ATA TAC GGG GAT GCC AAA AAC GGC GTG TTT AAT AAA GAT       1152
Ser Thr Ala Ile Tyr Gly Asp Ala Lys Asn Gly Val Phe Asn Lys Asp
        370                375                380

TAT GAT TTC GGG TTT GGA AAA GTG AGG CAG GTG AAG GAC TTG CAA ATG       1200
Tyr Asp Phe Gly Phe Gly Lys Val Arg Gln Val Lys Asp Leu Gln Met
385                390                395                400

GGA CTC CTT ATG TAT TTG GGC AAA CCA AAG                               1230
Gly Leu Leu Met Tyr Leu Gly Lys Pro Lys
                    405                410

(2) INFORMATION FOR SEQ ID NO:13:

(i) SEQUENCE CHARACTERISTICS:
        (A) LENGTH: 1230 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..1230

(ix) FEATURE:
        (A) NAME/KEY: mat_peptide
        (B) LOCATION: 1..465
        (D) OTHER INFORMATION: /product= "bFGF"

(ix) FEATURE:
        (A) NAME/KEY: mat_peptide
        (B) LOCATION: 472..1230
        (D) OTHER INFORMATION: /product= "Saporin"

(xi) SEQUENCE DESCRIPTION: SEQ ID NO:13:

ATG GCT GCT GGT TCT ATC ACT ACT CTG CCG GCT CTG CCG GAA GAC GGT        48
Met Ala Ala Gly Ser Ile Thr Thr Leu Pro Ala Leu Pro Glu Asp Gly
1               5                  10                 15

GGT TCT GGT GCT TTC CCG CCC GGC CAC TTC AAG GAC CCC AAG CGG CTG        96
Gly Ser Gly Ala Phe Pro Pro Gly His Phe Lys Asp Pro Lys Arg Leu
                20                 25                 30

TAC TGC AAA AAC GGG GGC TTC TTC CTG CGC ATC CAC CCC GAC GGC CGA       144
Tyr Cys Lys Asn Gly Gly Phe Phe Leu Arg Ile His Pro Asp Gly Arg
            35                 40                 45

GTT GAC GGG GTC CGG GAG AAG AGC GAC CCT CAC ATC AAG CTT CAA CTT       192
Val Asp Gly Val Arg Glu Lys Ser Asp Pro His Ile Lys Leu Gln Leu
        50                 55                 60

CAA GCA GAA GAG AGA GGA GTT GTG TCT ATC AAA GGA GTG TGT GCT AAC       240
Gln Ala Glu Glu Arg Gly Val Val Ser Ile Lys Gly Val Cys Ala Asn
65                 70                 75                 80

CGT TAC CTG GCT ATG AAG GAA GAT GGA AGA TTA CTG GCT TCT AAA TGT       288
Arg Tyr Leu Ala Met Lys Glu Asp Gly Arg Leu Leu Ala Ser Lys Cys
                85                 90                 95

GTT ACG GAT GAG TGT TTC TTT TTT GAA CGA TTG GAA TCT AAT AAC TAC       336
Val Thr Asp Glu Cys Phe Phe Phe Glu Arg Leu Glu Ser Asn Asn Tyr
            100                105                110

AAT ACT TAC CGG TCA AGG AAA TAC ACC AGT TGG TAT GTG GCA TTG AAA       384
Asn Thr Tyr Arg Ser Arg Lys Tyr Thr Ser Trp Tyr Val Ala Leu Lys
        115                120                125

CGA ACT GGG CAG TAT AAA CTT GGA TCC AAA ACA GGA CCT GGG CAG AAA       432
Arg Thr Gly Gln Tyr Lys Leu Gly Ser Lys Thr Gly Pro Gly Gln Lys
130                135                140
```

```
GCT ATA CTT TTT CTT CCA ATG TCT GCT AAG AGC GCC ATG GTC ACA TCA      480
Ala Ile Leu Phe Leu Pro Met Ser Ala Lys Ser Ala Met Val Thr Ser
145                 150                 155                 160

ATC ACA TTA GAT CTA GTA AAT CCG ACC GCG GGT CAA TAC TCA TCT TTT      528
Ile Thr Leu Asp Leu Val Asn Pro Thr Ala Gly Gln Tyr Ser Ser Phe
                165                 170                 175

GTG GAT AAA ATC CGA AAC AAC GTA AAG GAT CCA AAC CTG AAA TAC GGT      576
Val Asp Lys Ile Arg Asn Asn Val Lys Asp Pro Asn Leu Lys Tyr Gly
            180                 185                 190

GGT ACC GAC ATA GCC GTG ATA GGC CCA CCT TCT AAA GAA AAA TTC CTT      624
Gly Thr Asp Ile Ala Val Ile Gly Pro Pro Ser Lys Glu Lys Phe Leu
        195                 200                 205

AGA ATT AAT TTC CAA AGT TCC CGA GGA ACG GTC TCA CTT GGC CTA AAA      672
Arg Ile Asn Phe Gln Ser Ser Arg Gly Thr Val Ser Leu Gly Leu Lys
210                 215                 220

CGC GAT AAC TTG TAT GTG GTC GCG TAT CTT GCA ATG GAT AAC ACG AAT      720
Arg Asp Asn Leu Tyr Val Val Ala Tyr Leu Ala Met Asp Asn Thr Asn
225                 230                 235                 240

GTT AAT CGG GCA TAT TAC TTC AAA TCA GAA ATT ACT TCC GCC GAG TTA      768
Val Asn Arg Ala Tyr Tyr Phe Lys Ser Glu Ile Thr Ser Ala Glu Leu
                245                 250                 255

ACC GCC CTT TTC CCA GAG GCC ACA ACT GCA AAT CAG AAA GCT TTA GAA      816
Thr Ala Leu Phe Pro Glu Ala Thr Thr Ala Asn Gln Lys Ala Leu Glu
            260                 265                 270

TAC ACA GAA GAT TAT CAG TCG ATC GAA AAG AAT GCC CAG ATA ACA CAG      864
Tyr Thr Glu Asp Tyr Gln Ser Ile Glu Lys Asn Ala Gln Ile Thr Gln
        275                 280                 285

GGA GAT AAA AGT AGA AAA GAA CTC GGG TTG GGG ATC GAC TTA CTT TTG      912
Gly Asp Lys Ser Arg Lys Glu Leu Gly Leu Gly Ile Asp Leu Leu Leu
290                 295                 300

ACG TTC ATG GAA GCA GTG AAC AAG AAG GCA CGT GTG GTT AAA AAC GAA      960
Thr Phe Met Glu Ala Val Asn Lys Lys Ala Arg Val Val Lys Asn Glu
305                 310                 315                 320

GCT AGG TTT CTG CTT ATC GCT ATT CAA ATG ACA GCT GAG GTA GCA CGA     1008
Ala Arg Phe Leu Leu Ile Ala Ile Gln Met Thr Ala Glu Val Ala Arg
                325                 330                 335

TTT AGG TAC ATT CAA AAC TTG GTA ACT AAG AAC TTC CCC AAC AAG TTC     1056
Phe Arg Tyr Ile Gln Asn Leu Val Thr Lys Asn Phe Pro Asn Lys Phe
            340                 345                 350

GAC TCG GAT AAC AAG GTG ATT CAA TTT GAA GTC AGC TGG CGT AAG ATT     1104
Asp Ser Asp Asn Lys Val Ile Gln Phe Glu Val Ser Trp Arg Lys Ile
        355                 360                 365

TCT ACG GCA ATA TAC GGG GAT GCC AAA AAC GGC GTG TTT AAT AAA GAT     1152
Ser Thr Ala Ile Tyr Gly Asp Ala Lys Asn Gly Val Phe Asn Lys Asp
370                 375                 380

TAT GAT TTC GGG TTT GGA AAA GTG AGG CAG GTG AAG GAC TTG CAA ATG     1200
Tyr Asp Phe Gly Phe Gly Lys Val Arg Gln Val Lys Asp Leu Gln Met
385                 390                 395                 400

GGA CTC CTT ATG TAT TTG GGC AAA CCA AAG                             1230
Gly Leu Leu Met Tyr Leu Gly Lys Pro Lys
                405                 410

(2) INFORMATION FOR SEQ ID NO:14:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)
```

-continued

```
    (xi) SEQUENCE DESCRIPTION: SEQ ID NO:14:

AATTCCCCTG TTGACAATTA ATCATCGAAC TAGTTAACTA GTACGCAGCT TGGCTGCAG       59

(2) INFORMATION FOR SEQ ID NO:15:

(i) SEQUENCE CHARACTERISTICS:
          (A) LENGTH: 59 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:15:

GTCGACCAAG CTTGGGCATA CATTCAATCA ATTGTTATCT AAGGAAATAC TTACATATG       59
```